(12) United States Patent
Steinmetz

(10) Patent No.: US 10,561,730 B2
(45) Date of Patent: *Feb. 18, 2020

(54) PLANT VIRUS PARTICLES FOR DELIVERY OF PHOTOSENSITIVE AGENTS

(71) Applicant: CASE WESTERN RESERVE UNIVERSITY, Cleveland, OH (US)

(72) Inventor: Nicole F. Steinmetz, San Diego, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,549

(22) Filed: Dec. 18, 2018

(65) Prior Publication Data

US 2019/0175733 A1 Jun. 13, 2019

Related U.S. Application Data

(63) Continuation of application No. 15/403,692, filed on Jan. 11, 2017, now Pat. No. 10,159,736.

(60) Provisional application No. 62/277,135, filed on Jan. 11, 2016.

(51) Int. Cl.

| C12N 7/00 | (2006.01) |
| A61K 45/06 | (2006.01) |
| A61K 31/555 | (2006.01) |
| A61K 41/00 | (2020.01) |
| A61K 47/69 | (2017.01) |

(52) U.S. Cl.
CPC ........ *A61K 41/0071* (2013.01); *A61K 31/555* (2013.01); *A61K 45/06* (2013.01); *A61K 47/6901* (2017.08); *C12N 7/00* (2013.01); *C12N 2770/00023* (2013.01); *C12N 2770/00032* (2013.01); *C12N 2770/00042* (2013.01)

(58) Field of Classification Search
None
See application file for complete search history.

(56) References Cited

FOREIGN PATENT DOCUMENTS

WO 2013181557 A1 12/2013

OTHER PUBLICATIONS

Brasch et al. Encapsulation of Phthalocyanine Supramolecular Stacks into Virus-like Particles. J. Am. Chem. Soc. 2011, 133, 6878-6881.*
Wu et al. Viruses as self-assembled nanocontainers for encapsulation of functional cargoes. Korean J. Chem. Eng., 30(7), 1359-1367 (2013).*
Rapozzi et al. Anticancer activity of cationic porphyrins in melanoma tumour-bearing mice and mechanistic in vitro studies. Molecular Cancer 2014, 13:75.*
Wen, Amy M., et al. "Utilizing viral nanoparticle/dendron hybrid conjugates in photodynamic therapy for dual delivery to macrophages and cancer cells." Bioconjugate chemistry 27.5 (2016): 1227.
Mallidi, Srivalleesha, et al. "Beyond the Barriers of Light Penetration: Strategies, Perspectives and Possibilities for Photodynamic Therapy" Theranostics 6.13 (2016): 2458.
Allison, Ron R., et al. "Photosensitizers in clinical PDT." Photodiagnosis and Photodynamic Therapy 1.1 (2004): 27-42.
Wen, Amy M. et al. "Photodynamic Activity of Viral Nanoparticles Conjugated with C60." Chemical communications (Cambridge, England) 48.72 (2012): 9044-9046. PMC. Web. Apr. 24, 2017.
Rhee J-K, Baksh M, Nycholat C, Paulson JC, Kitagishi H, Finn MG. Glycan-Targeted Virus-like Nanoparticles for Photodynamic Therapy. Biomacromolecules. 2012;13(8):2333-2338. doi:10.1021/bm300578p.
Steinmetz NF, Cho C-F, Ablack A, Lewis JD, Manchester M. Cowpea mosaic virus nanoparticles target surface vimentin on cancer cells. Nanomedicine (London, England). 2011;6(2):351-364. doi:10.2217/nnm.10.136.
Agrawal A, Manchester M. Differential uptake of chemically modified Cowpea mosaic virus nanoparticles in macrophage subpopulations present in inflammatory and tumor microenvironments. Biomacromolecules. 2012;13(10):3320-3326. doi:10.1021/bm3010885.
Lee, Karin L., et al. "High aspect ratio nanotubes formed by tobacco mosaic virus for delivery of photodynamic agents targeting melanoma." ACS Biomaterials Science & Engineering 2.5 (2016): 838-844.
Cui, Liyang, et al. "A PEGylation-free biomimetic porphyrin nanoplatform for personalized cancer theranostics." ACS nano 94 (2015): 4484-4495.
Pokorski JK, Steinmetz NF. The Art of Engineering Viral Nanoparticles. Molecular pharmaceutics. 2011;8(1):29-43. doi:10.1021/mp100225y.
Wen Am, Shukla S. Saxena P, et al. Interior engineering of a viral nanoparticle and its tumor homing properties. Biomacromolecules. 2012;13(12):3990-4001. doi:10.1021/bm301278f.
Wang, Qian, et al. "Natural supramolecular building blocks: wild-type cowpea mosaic virus." Chemistry & biology 9.7 (2002): 805-811.
Lizotte PH, Wen Am, Sheen MR, et al. In situ vaccination with cowpea mosaic virus nanoparticles suppresses metastatic cancer. Nature nanotechnology. 2016;11(3):295-303. doi:10.1038/nnano.2015.292.
Singh P, Prasuhn D, Yeh RM, et al. Bio-distribution, toxicity and pathology of cowpea mosaic virus nanoparticles in vivo. Journal of controlled release: official journal of the Controlled Release Society. 2007;120(1-2):41-50. doi:10.1016/j.jconrel.2007.04.003.

(Continued)

*Primary Examiner* — Nianxiang Zou
(74) *Attorney, Agent, or Firm* — Tarolli, Sundheim, Covell & Tummino LLP

(57) ABSTRACT

Photodynamic virus particles including a plant virus particle associated with a photosensitizing agent are described. Methods of treating cancer in a subject by administering to the subject a therapeutically effective amount of the photodynamic virus particles and illuminating a cancer-bearing region of the subject to activate the photodynamic virus particles are also described.

9 Claims, 8 Drawing Sheets

(56) References Cited

OTHER PUBLICATIONS

Feese, Elke, et al. "Photobactericidal porphyrin-cellulose nanocrystals: synthesis, characterization, and antimicrobial properties." Biomacromolecules 12.10 (2011): 3528-3539.

Bruckman MA, Randolph LN, VanMeter A, et al. Biodistribution, pharmacokinetics, and blood compatibility of native and PEGylated tobacco mosaic virus nano-rods and -spheres in mice. Virology. 2014;449:163-173. doi:10.1016/j.virol.2013.10.035.

Carpenter, Bradley L., et al. "Synthesis, characterization, and antimicrobial efficacy of photomicrobicidal cellulose paper." Biomacromolecules 16.8 (2015): 2482-2492.

Pavani, Christiane, et al. "Effect of zinc insertion and hydrophobicity on the membrane interactions and PDT activity of porphyrin photosensitizers." Photochem. Photobiol. Sci 8 (2009): 233-240.

Demir, Mukerrem, and Michael HB Stowell. "A chemoselective biomolecular template for assembling diverse nanotubular materials." Nanotechnology 13 (2002): 541-544.

Bruckman MA, Steinmetz NF. Chemical Modification of the Inner and Outer Surfaces of Tobacco Mosaic Virus (TMV). Methods in molecular biology (Clifton, NJ). 2014;1108:173-185. doi:10.1007/978-1-62703-751-8_13.

Wen AM, Infusino M, De Luca A, et al. Interface of Physics and Biology: Engineering Virus-Based Nanoparticles for Biophotonics. Bioconjugate Chemistry. 2015;26(1):51-62. doi:10.1021/bc500524f.

Bruckman, Michael A., et al. "Surface modification of tobacco mosaic virus with "click" chemistry." ChemBioChem 9.4 (2008): 519-523.

Brasch, et al. "Encapsulation of Phthalocyanine Supramolecular Stacks into Virus-like Particles", J. Am. Chen. Soc. 2011, 133, 6878-6881.

\* cited by examiner

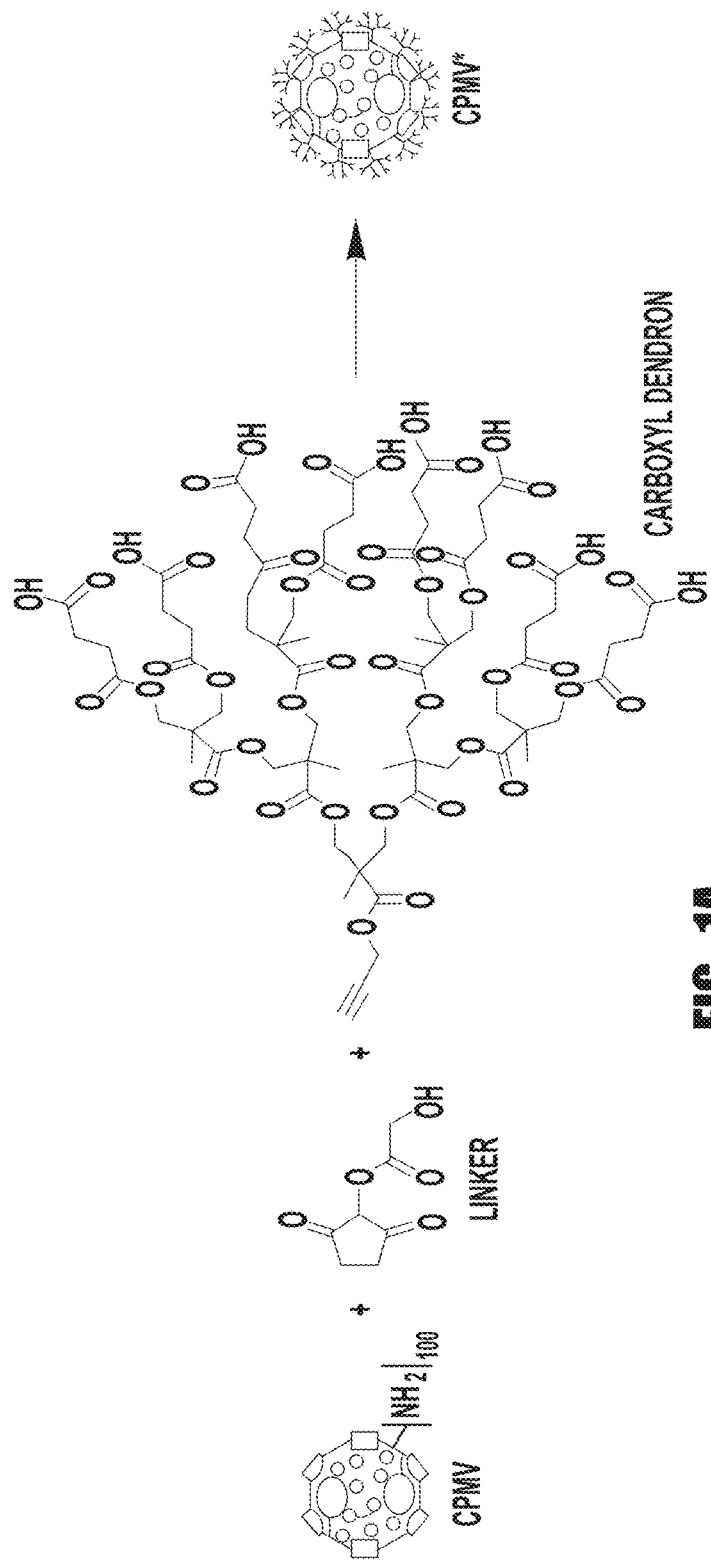
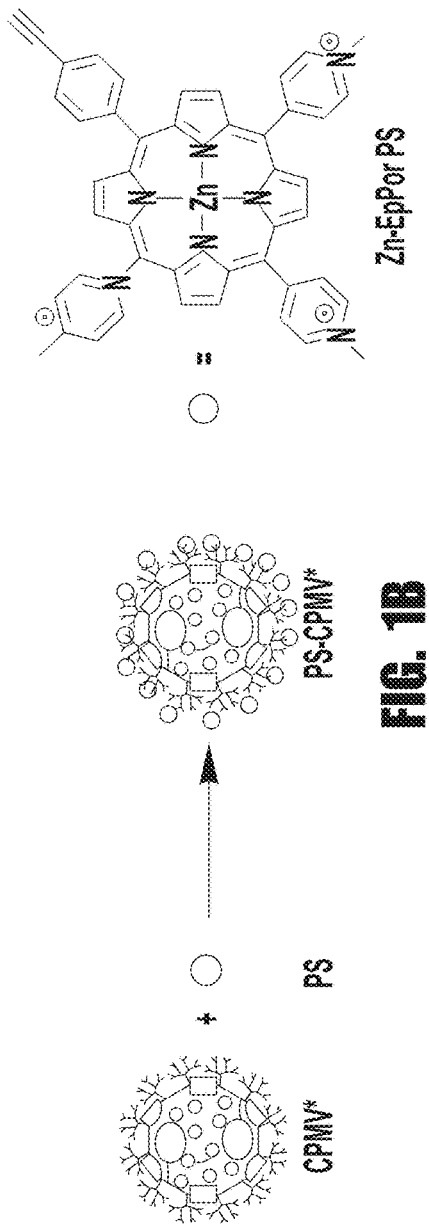
FIG. 1A
FIG. 1B

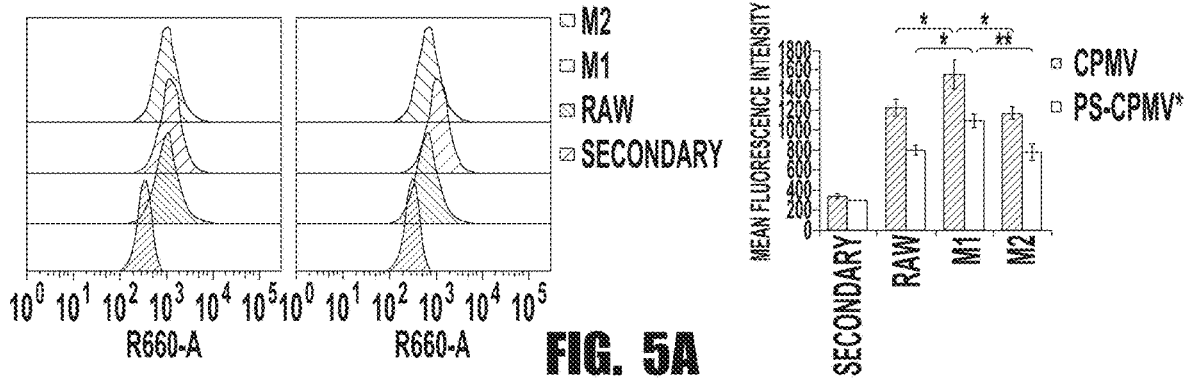
FIG. 5A
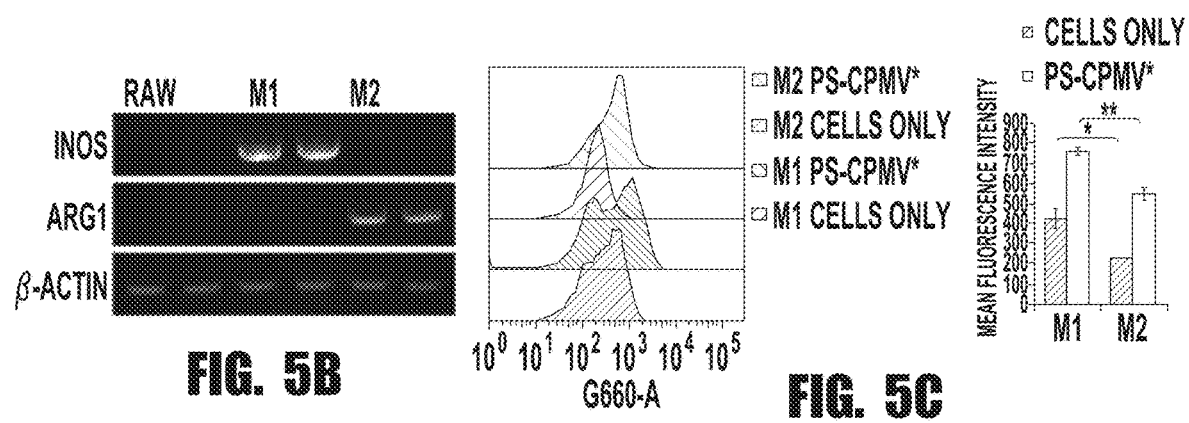
FIG. 5B
FIG. 5C
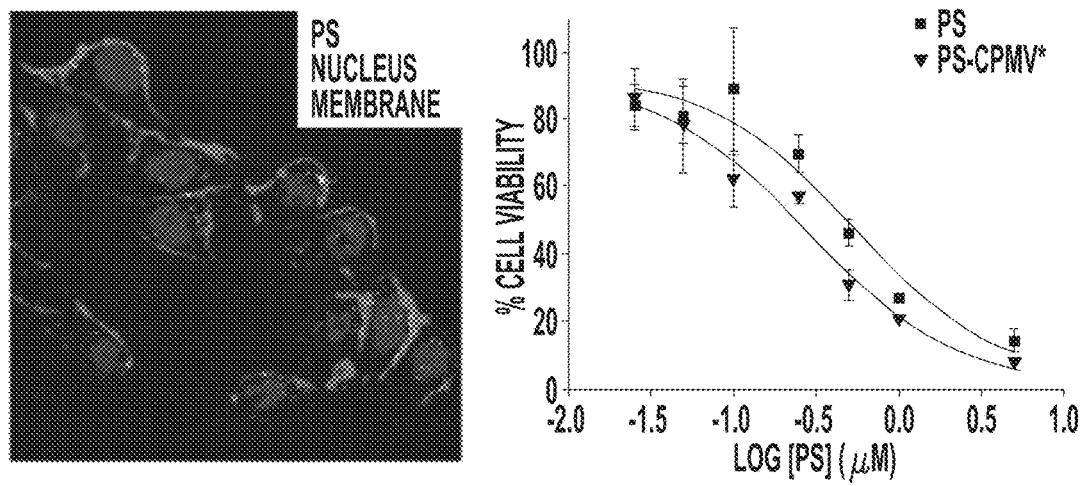
FIG. 6A
FIG. 6B

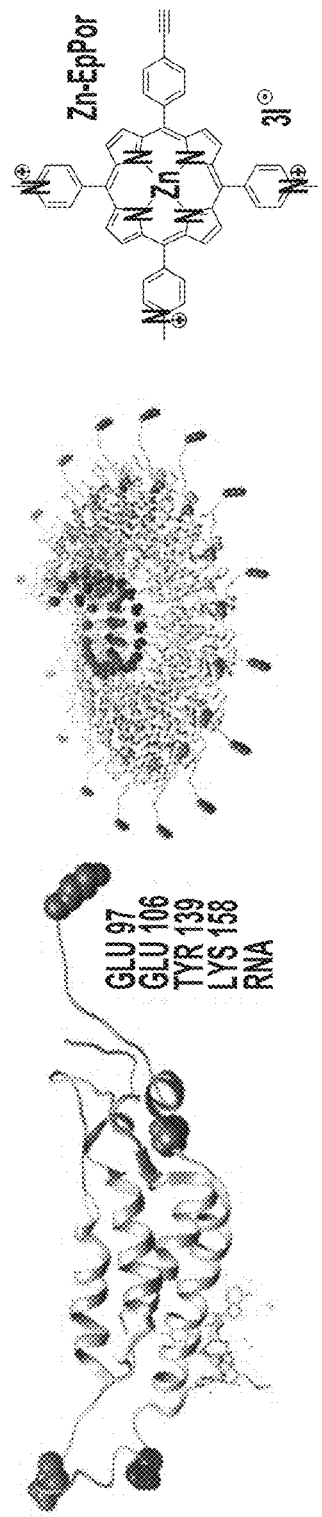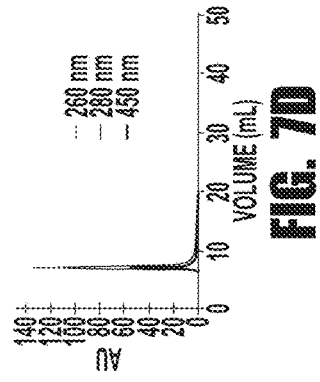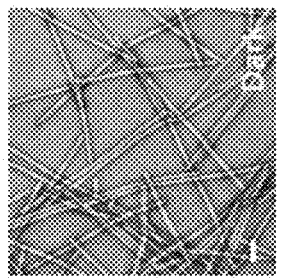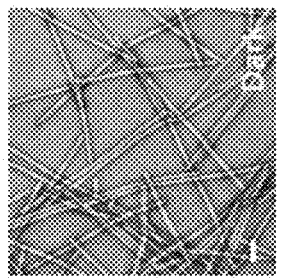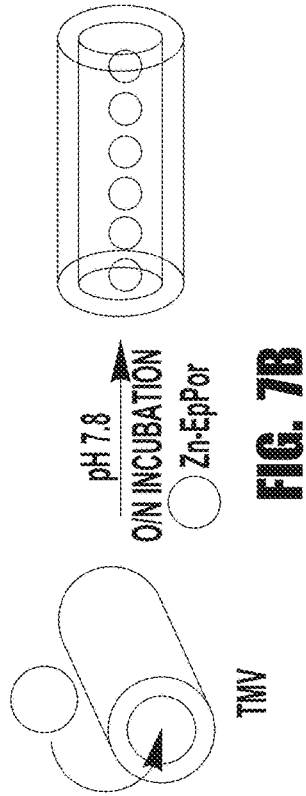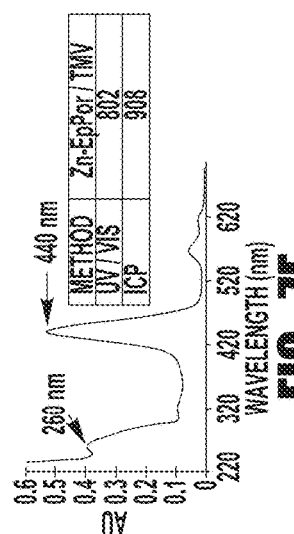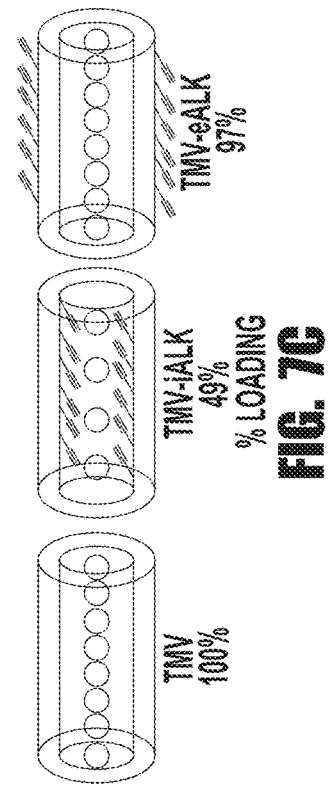

NUCLEI
MEMBRANE
Zn-EpPor$^{TMV}$

PLANT VIRUS PARTICLES FOR DELIVERY OF PHOTOSENSITIVE AGENTS

CROSS-REFERENCE TO RELATED APPLICATIONS

This application claims priority to U.S. Provisional Application Ser. No. 62/277,135, filed on Jan. 11, 2016, the disclosure of which is hereby incorporated by reference in its entirety.

GOVERNMENT FUNDING

The present invention was made with Government support under Grant No. CMMI NM 333651 from the National Science Foundation, and Grant Nos. F31HL129703 and T32EB007509 from the National Institutes of Health. The Government has certain rights in the invention.

BACKGROUND

Photodynamic therapy (PDT) is a minimally invasive therapy for the localized treatment of fairly shallow tumors that only requires the presence of a photosensitizer, a light source, and oxygen. The photochemical reaction of light with the photosensitizer results in the formation of reactive oxygen species that induce localized cell killing. Due to spatial control using light application, treatment is limited to a specific area, which can result in fewer systemic effects, greater efficacy, and more cost-effectiveness compared to chemotherapy. However, several significant challenges often limit the practical application of PDT, including poor bioavailability and low accumulation in the tumor tissue, dispersal of the photosensitizer throughout the body necessitating avoidance of sunlight for several weeks following treatment, and the hydrophobic nature of most photosensitizers, making them insoluble in physiological conditions. Agostinis et al., CA Cancer J Clin., 61, 250-281 (2011).

To overcome these challenges, the use of a nanoparticle delivery vehicle for photosensitizers is a potentially advantageous development in PDT due to several benefits, including greater payload delivery that is specific to cancer cells due to both passive and active targeting methods, reduction of toxicity of many hydrophobic photosensitizers that tend to form colloidal aggregates, and prevention of drug inactivation by plasma components. Lucky et al., Chem Rev., 115, 1990-2042 (2015). Plant viruses in particular are useful as delivery vehicles due to their ease of manufacture, monodispersity, biocompatibility, and good safety profile. Manchester M, Singh P., Adv Drug Delivery Rev., 58, 1505-1522 (2006). Viruses have been explored for PDT, with applications shown in the treatment of leukemia T cells (Stephanopoulos et al., ACS Nano., 4, 6014-6020 (2010)), prostate cancer cells (Wen et al., Chem Commun (Cambridge, U K), 48, 9044-9046 (2012)) and CD22+ cells (Rhee et al., Biomacromolecules, 13, 2333-2338 (2012)), as well as for antimicrobial therapy.

As a virus-based delivery vehicle for anticancer applications, the 30-nm-sized icosahedron cowpea mosaic virus (CPMV) is particularly noteworthy as it possesses a natural affinity to cancer cells that results from its specificity for and interaction with surface expressed vimentin. Steinmetz et al., Nanomedicine, 6, 351-364 (2011). Furthermore, it has been demonstrated that CPMV has a preference for immune cells, specifically the M2 subpopulation of macrophages, although the mechanism behind this partitioning has not yet been elucidated. Agrawal A, Manchester M., Biomacromolecules, 13, 3320-3326 (2012). The tumor microenvironment is diverse and consists of more than just cancer cells, and macrophages in particular are a major component as well. Whereas the classical M1 macrophages are involved in immune activation and tumor suppression, there is increasing evidence that tumor-associated macrophages are of an M2 polarization and play a role in the promotion of tumor progression and invasion. Sica et al., Eur J Cancer, 42, 717-727 (2006). The implication of M2 macrophages in suppressing an antitumor immune response makes them a good target for therapy. The elimination of tumor cells together with M2 macrophages has the potential to stimulate the immune system toward destroying any remnant malignant cells. Targeting tumor-associated macrophages in general has resulted in greater nanoparticle accumulation and higher efficacy, allowing them to serve as "drug depots" for delivering drugs such as platinum-based chemotherapies to surrounding cancer cells. Miller et al., Nat Commun., 6, 8692 (2015).

A novel photosensitizing drug that has been developed for bactericidal applications, and only recently explored for its use in cancer therapy (Lee et al., "High-aspect ratio nanotubes formed by tobacco mosaic virus for delivery of photodynamic agents targeting melanoma" ACS Biomater Sci Eng. 2016) is a zinc ethynylphenyl porphyrin (Zn-EpPor) photosensitizer (PS). Porphyrin compounds are commonly applied for PDT (Cui et al., ACS Nano., 9, 4484-4495 (2015)) and the most widely used photosensitizer in the clinic, Photofrin, is composed of porphyrin subunits. PS is unique in that it possesses a positive charge that assists in preferential accumulation in tumor tissue, and its porphyrin ring contains a zinc atom that enhances membrane binding efficiency, both of which makes the photosensitizer more potent.

SUMMARY

Photodynamic therapy (PDT) is a promising avenue for greater treatment efficacy of cancer such as highly resistant and aggressive melanoma. Through photosensitizer attachment to nanoparticles, specificity of delivery can be conferred to further reduce potential side effects. While the main focus of PDT is the destruction of cancer cells, additional targeting of tumor-associated macrophages also present in the tumor microenvironment could further enhance treatment by eliminating their role in processes such as invasion, metastasis, and immunosuppression. The inventors have investigated PDT of macrophages and tumor cells through delivery using the natural noninfectious nanoparticle cowpea mosaic virus (CPMV), which has been shown to have specificity for the immunosuppressive subpopulation of macrophages and also targets cancer cells. They further explored conjugation of CPMV/dendron hybrids in order to improve the drug loading capacity of the nanocarrier. The inventors demonstrated effective elimination of both macrophage and tumor cells at low micromolar concentrations of the photosensitizer when delivered with the CPMV bioconjugate, thereby potentially improving melanoma treatment.

In one aspect, the present invention provides a photodynamic virus particle, comprising a plant virus particle associated with a photosensitizing agent. In some embodiments, the plant virus particle is a filamentous plant virus particle. In other embodiments, the plant virus particle is an icosahedral plant virus particle (e.g, a cowpea mosaic virus particle). In additional embodiments, the plant virus particle is a rod-shaped plant virus particle (e.g, a tobacco mosaic virus). In further embodiments, the photosensitizing agent is a porphyrin compound (e.g., zinc ethynyl porphyrin).

The photosensitizing agent can be associated with the plant virus particle in a variety of different ways. In some embodiments, the photosensitizing agent is associated with the plant virus particle through electrostatic interaction. In further embodiments, the photosensitizing agent is associated to the interior of the virus particle. In yet further embodiments, the photosensitizing agent is covalently linked to the plant virus particle. In some embodiments, the photosensitizing agent is associated with the plant virus particle through a carboxyl dendron polymer.

In another aspect, the invention provides a method of treating cancer in a subject by administering to the subject a therapeutically effective amount of photodynamic virus particles comprising a plant virus particle associated with a photosensitizing agent, and illuminating a cancer-bearing region of the subject to activate the photodynamic virus particles. In some embodiments, the cancer is skin cancer, while in further embodiments, the cancer is melanoma. In some embodiments, the photodynamic virus particle is administered together with a pharmaceutically acceptable carrier. In other embodiments, the method further comprises treatment of the subject with an additional type of anticancer therapy.

BRIEF DESCRIPTION OF THE FIGURES

The present invention may be more readily understood by reference to the following drawings.

FIGS. 1A-1B provide a schematic of carboxyl dendron conjugation and PS attachment. (a) Alkyne-functionalized carboxyl dendrons were attached to CPMV using an intervening azide linker. (b) Zn-EpPor PS was then incorporated through electrostatic interactions with the dendrons. Structure of PS is shown in insert on right.

FIGS. 5A-5C provides graphs and images showing macrophage polarization and comparison of CPMV association. (a) Flow cytometry analysis of CPMV and PS-CPMV* association with polarized macrophages show increased signal in M1 macrophages. Particles were stained using a rabbit anti-CPMV antibody followed by a secondary Alexa Fluor 647-labeled anti-rabbit antibody. Secondary only staining was used as the control, with similar results observed for cells without staining. Histograms are shown to the left, and quantification of mean fluorescence intensity is shown to the right. For the bar graphs, data for CPMV are shown as solid bars, while PS-CPMV* data are checkered, and statistical significance is indicated by asterisks (*p<0.05, **p<0.01). (b) RAW 264.7 macrophage cells were polarized with treatment with either LPS and IFN-γ or IL-4 and verified by RT-PCR analysis for increased iNOS and Arg1 expression for M1 and M2 polarization, respectively. Treatment was performed in duplicate. Untreated cells were analyzed for comparison, and β-actin served as a loading control. (c) Flow cytometry analysis of PS-CPMV* uptake based on PS signal also revealed increased fluorescence in M1 macrophages compared to M2 macrophages. Histograms are shown to the left, and quantification of mean fluorescence intensity is shown to the right. For the bar graphs, cells only data are shown as solid bars, while PS-CPMV* data are checkered. Statistical significance is indicated by asterisks (*p<0.05, **p<0.01).

FIGS. 6A and 6B provide a graph and image showing uptake and cell killing in B16F10 melanoma cell line. (a) Confocal microscopy of cells incubated with PS-CPMV* showed PS uptake. The nucleus is shown (DAPI) as well as the cell membrane (Alexa Fluor 488-labeled WGA). (b) MTT cell viability assay of cells after 8 h of particle uptake and white light illumination for half an hour revealed a slight increase in cell killing efficacy for particulate delivery of PS. Free PS had a $IC_{50}$ of 0.54 µM, while PS-CPMV* had an $IC_{50}$ of 0.28 µM.

FIGS. 7A-7F provide schemes, graphs, and images showing $_{Zn-EpPor}$TMV conjugation and characterization. (A) (left) Lysine mutant TMV coat protein (T158K) Glu97, Glu 106, Tyr 139, Lys 158, RNA and (right) Zn-EpPor structure; (B) Schematic of Zn-EpPor loading into TMV; (C) Schematic of Zn-EpPor loading efficiencies after interior and exterior modification with alkynes at which amino acid Glu97 and Glu106 (interior) and Tyr 139 (exterior); (D) Size exclusion chromatography of $_{Zn-EpPor}$TMV shows co-elution of intact TMV (260 and 280 nm) and Zn-EpPor specific absorbance (440 nm) at the retention time of 8 mL; (e) UV/visible spectroscopy of $_{Zn-EpPor}$TMV, table inset shows quantification of Zn-EpPor loading comparing UV/visible spectroscopy and ICP-OES measurements; (f) Negatively stained TEM images of $_{Zn-EpPor}$TMV after light exposure for 30 minutes (top) and corresponding dark control (bottom).

DETAILED DESCRIPTION

Figure 2A:
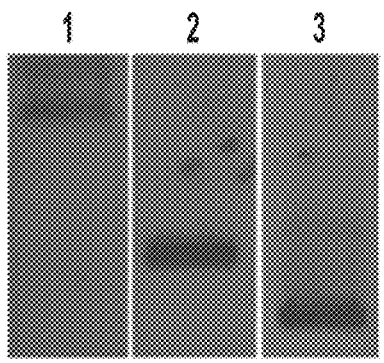
FIGS. 2A-2D provide graphs and images providing characterization of modified particles. (a) Native agarose gel of CPMV, CPMV-$N_3$, and CPMV* showed expected shifts in band mobility due to increasing negative charge of the modified particles. 1=CPMV; 2=CPMV-$N_3$; 3=CPMV*. (b) SDS gel electrophoresis revealed additional density (arrows) for CPMV* above the unmodified coat protein bands due to attachment of carboxyl dendrons, with about 45% modification based on densitometric analysis. CPMV consists of 60 copies of a small 24 kDa and a large 42 kDa coat protein. M=SeeBlue Plus2 molecular weight marker. (c) TEM images of CPMV* and PS-CPMV* demonstrates particle integrity after modification. (d) UV/visible spectroscopy of PS-CPMV and PS-CPMV* showed enhanced interaction of PS with CPMV* compared to CPMV.
Figure 2B:
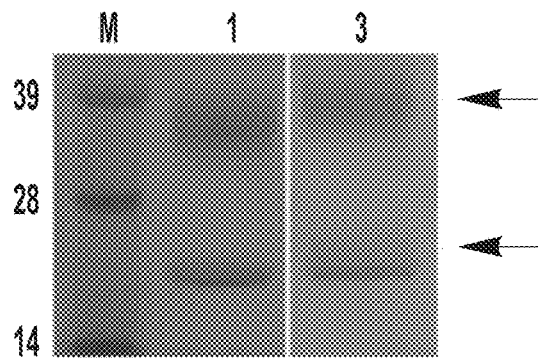
Figure 2C:
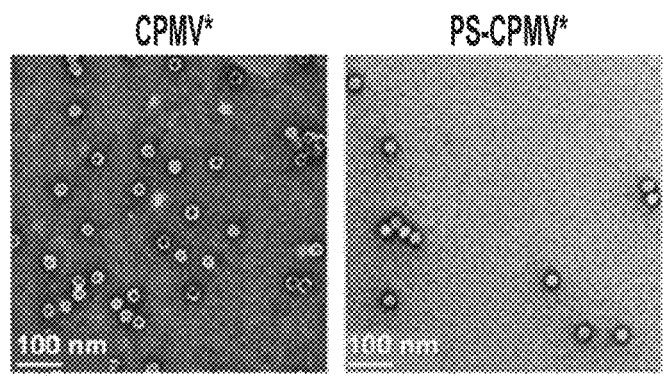
Figure 2D:
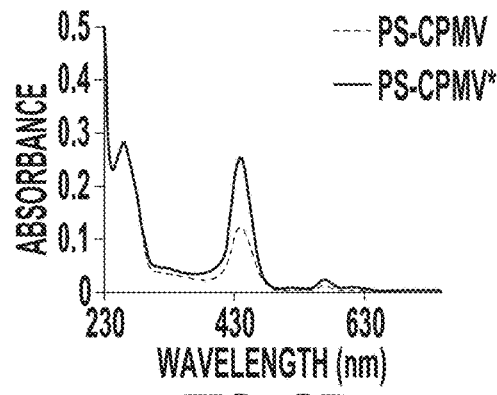

The present invention provides photodynamic virus particles that are plant virus particle associated with a photosensitizing agent. In an additional aspect of the invention, a therapeutically effective amount of a photodynamic virus particle is administered to a subject to provide a method of treating cancer.

Definitions

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a virus particle" includes a combination of two or more virus particles, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Treat", "treating", and "treatment", etc., as used herein, refer to any action providing a benefit to a subject afflicted with a condition or disease such as melanoma, including improvement in the condition through lessening or suppression of at least one symptom, delay in progression of the disease, etc.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

In one aspect, the present invention provides a photodynamic virus particle, comprising a plant virus particle associated with a photosensitizing agent. Associating a plant virus particle with the photosensitizing agent provides a number of advantages for photodynamic therapy. Advantages can include increased biocompatibility and superior biodistribution, which can include higher levels of accumulation in tumor cells and cancer-associated cells such as M2 macrophages. Various plant virus particles, photosensizing agents, and methods of associating the two are described herein.

Plant Viruses

The photodynamic virus particles of the present invention are based on plant virus particles. Plant virus particles preferably grow in plants, and have the advantages of being readily cultivated, and are unlikely to cause infection when used in vivo in a subject. Plant virus particles are categorized based on their source and structure. In various embodiments, virus particles having an icosahedral, filamentous, or rod-shaped structure can be used. Preferably, the virus particles used are non-enveloped virus particles. Use of photodynamic plant virus particles is preferred, in part as a result of the proclivity of these viral particles to be taken up by diseased tissue.

A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm. Filament-like virus particles are flexible in addition to being long and thin, and therefore some embodiments of the invention are directed to use of a flexible filamentous plant virus. As described herein, use of filamentous plant viruses provides the advantages of improved tumor targeting and penetration. Embodiments of the invention can deliver about 10%, about 20%, about 30%, about 40%, or even about 50% or more of the injected dose to tumor tissue.

In some embodiments, the filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus*, and *Sclerodamavirus*. In some embodiments, the filamentous plant virus belongs to the genus *Potexvirus*. In further embodiments, the filamentous plant virus belongs to the Potato Virus X species.

In some embodiments, the photodynamic virus particle is based on a rod-shaped plant virus. A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus *Furovirus, Hordevirus, Pecluvirus, Pomovirus, Tobamovirus*, and *Tobravirus*. In some embodiments, the rod-shaped plant virus belongs to the genus Tobamovirus. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

In some embodiments, the plant virus is an icosahedral plant virus. Examples of icosahedral plant viruses include the virus families Geminiviridae, Luteoviridae, Bromoviridae, Phycodnaviridae, and Picornaviridae. In some embodiments, the icosahedral plan virus is from the family Picornaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus *comovirus*. A preferred example of a *comovirus* is the cowpea mosaic virus particles.

Plant virus particles have an interior and an exterior. The exterior of a plant virus particle is the portion of the virus particle that is directly exposed to the environment. The interior of the plant virus particle is the portion of the virus particle that typically is adjacent to the genomic material within the virus particle, and is not directly exposed to the environment. In some embodiments, the plant virus particles are genetically modified to have one or more additional attachment sites on the interior or exterior of the plant virus particle. For example, the interior or exterior of the plant virus particle can be modified to include one or more additional lysine residues.

Plant virus particles can be obtained according to various methods known to those skilled in the art. In embodiments where plant virus particles are used, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

Photosensitizing Compounds

The present invention provides a photodynamic virus particle that includes a photosensitizing agent. A wide variety of photosensitizing agents are known to those skilled in the art, and are suitable for use in the present invention. Photosensitizing compounds have the ability to preferentially accumulate in diseased tissue and induce a therapeutic effect via the generation of cytotoxic species upon exposure to light. Classes of photosensitizing agents include porphyrins, chlorophylls and dyes. Allison, R R; et al., "Photosensitizers in clinical PDT," Photodiagnosis and Photodynamic Therapy. Elsevier. 1: 27-42 ((2004).

In some embodiments, the photosensitizing agent is a porphyrin compound. Porphyrins are a group of naturally occurring and intensely colored compounds, and are tetrapyrrolic molecules based on a heterocyclic macrocycle skeleton, known as a porphine. The fundamental porphine frame consists of four pyrrolic sub-units linked on opposing sides ($\alpha$-positions, numbered 1, 4, 6, 9, 11, 14, 16 and 19) through four methine (CH) bridges (5, 10, 15 and 20), known as the meso-carbon atoms/positions. The resulting conjugated planar macrocycle may be substituted at the meso- and/or $\beta$-positions (2, 3, 7, 8, 12, 13, 17 and 18). When the meso- and $\beta$-hydrogens are substituted with non-hydrogen atoms or groups, the resulting compounds are known as porphyrins. Porphyrin's highly conjugated skeleton produces a characteristic ultra-violet visible (UV-VIS) spectrum. The spectrum typically consists of an intense, narrow absorption band ($\varepsilon$>200000 1 mol$^{-1}$ cm$^{-1}$) at around 400 nm, followed by four longer wavelengths (450-700 nm). Examples of porphyrin photosensitizing agents include lutetium texaphyrin (Lutex™), 9-Acetoxy-2,7,12,17-tetrakis-($\beta$-methoxyethyl)-porphycene, Benzoporphyrin derivative monoacid ring A (Visudyne™), porfimir sodium (Photofrin™) temoporfin (Foscan™), and talaporfin (Laserphyrin™). In some embodiments, the photosensitizing agent is zinc ethynyl porphyrin.

Phthalocyanines (PCs) are another type of photosensitizing agents related to porphyrins. Instead of four bridging carbon atoms at the meso-positions, as for the porphyrins, PCs have four nitrogen atoms linking the pyrrolic sub-units. Phthalocyanines are azaporphyrins consisting of four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy is described in International Publication WO 2005/099689. Phthalocyanines strongly absorb clinically useful red or near IR radiation with absorption peaks falling between about 600 and 810 nm, which potentially allows deep penetration of tissue by the light.

Association of Photosensitizing Agents with the Plant Virus Particles

The present invention provides a photodynamic virus particle, comprising a plant virus particle associated with a photosensitizing agent. The photosensitizing agent can be associated to either the interior of the plant virus particle, the exterior of the plant virus particle, or to both the interior and exterior of the plant virus particle. Association of the photosensitizing agent with the plant virus particle includes both covalent linking of the photosensitizing agent to the plant virus particle, as well as other forms of association such as an electrostatic association. When a covalent linkage is used, the photosensitizing agent is linked to the plant virus particle by being chemical bonded to the plant virus particle. The linkage can be either direct or indirect, where indirect linkage is through an intermediate linking molecule.

In general, photosensitizing agents can be associated with the plant virus particles by any suitable technique, with appropriate consideration of the need for pharmacokinetic stability and reduced overall toxicity to the patient. Association of the agent to the virus should be subject to the single limitation that the nature and size of the agent and the site at which it is associated to the virus particle should not interfere with the biodistribution of the modified virus.

In some embodiments, the photosensitizing agent is associated with the plant virus particle using a non-covalent method of attachment. Non-covalent interaction differs from a covalent bond in that it does not involve the sharing of electrons, but rather involves more dispersed variations of electromagnetic interactions between molecules. Non-covalent interactions include electrostatic, π-effects, van der Waals forces, and hydrophobic effects. For example, electrostatic effects can be used to associate charged photosensitizing agents to oppositely charged surfaces inside or outside of a virus particle. For example, in some embodiments, a positively charged photosensitizing agent is associated to the interior of a virus particle (e.g., a rod-shaped virus particle) lined with a plurality of negative charges.

A photosensitizing agent can be coupled to a plant virus particle either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). In addition, genetic modification can be applied to introduce any desired functional residue, including non-natural amino acids, e.g. alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the agent or the virus particle, and thus increase the coupling efficiency. Preferred groups suitable for attaching agents to virus particles are lysine residues present in the viral coat protein. Suitable linkage chemistries include maleimidyl linkers and alkyl halide linkers and succinimidyl (e.g., N-hydroxysuccinimidyl (NHS)) linkers (which react with a primary amine on the plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional, can be employed as a linker group. Coupling can be affected, for example, through amino groups, carboxyl groups, sulfhydryl groups or oxidized carbohydrate residues.

A chemical linker can be used that is covalently bonded to both the photosensitizing agent and the plant virus particle. However, in some embodiments, the linker is used to facilitate a non-covalent association between the photosensitizing agent and the plant virus particle. An example of linkers that can be covalently linked to the virus particle, while providing an electrostatic association to a positively charged photosensitizing agent include negatively charged polymers such as dendron linkers. A dendron is a tree-shaped polymer, which provides a single point of attachment at one end, while being extensively branched at the other end, to provide a large number of possible attachment points. For example, the single point attachment end can include an amine, cysteine, or alkene for covalent attachment to the surface of the virus particle (which can include an additional linker molecule to facilitate this attachment), while the branched end can include organic groups conferring an overall ionic charge or hydrophilic or hydrophobic character suitable for creating affinity to a desired photosensitizing agent. An example of a suitable dendron linker includes a carboxyl dendron formed through a ring opening reaction of succinic anhydride. Accordingly, in some embodiments, the photosensitizing agent is associated with the plant virus particle through a carboxyl dendron polymer. A wide variety of dendron molecules are commercially available, or can be readily synthesized by one skilled in the art. For example, dendron molecules can be assembled using click chemistry employing Diels-Alder reactions, thiol-ene and thiol-yne reactions, and azide-alkyne reactions. A number of different polyester bis-MPA dendrons are commercially available through Sigma Aldritch.

Typically a plurality of photosensitizing agents are associated with each plant virus particle. The number of photosensitizing agents associated with the plant virus particle varies depending on the nature of the virus particle, the photosensitizing agent, and the method used to associate the two. It is typically desirable to associate as many photosensitizing agents with the virus particle as possible to increase the activity of the individual virus particles. In some embodiments, each plant virus particle is associated with an average of at least about 5 photosensitizing agents, at least about 10 photosensitizing agents, at least about 20 photosensitizing agents, at least about 50 photosensitizing agents, at least about 100 photosensitizing agents, or at least about 200 photosensitizing agents.

Photodynamic Therapy

In one aspect, the present invention provides a method of treating cancer in a subject by administering to the subject a therapeutically effective amount of photodynamic virus particles comprising a plant virus particle associated with a photosensitizing agent, and illuminating a cancer-bearing region of the subject to activate the photodynamic virus particles. Activating a photosensitizing agent by light to treat a disease or condition is referred to as photodynamic therapy. A cancer-bearing region can be a tumor, or a region of tissue including cancer cells. For example, when treating skin cancer, the cancer-bearing region can be a region of skin including a tumor. The photodynamic virus particle used in the photodynamic therapy can have any of the features described herein.

Photodynamic therapy (PDT) is a form of phototherapy involving light and a photosensitizing chemical substance, used in conjunction with molecular oxygen to elicit cell death as a result of phototoxicity. See Mallidi et al, Theranostics, 6(13), 2458-2487 (2016). PDT applications involve three components: a photosensitizer, a light source and tissue oxygen. The wavelength of the light source should be appropriate for exciting the photosensitizer to produce radicals and/or reactive oxygen species. These are free radicals (Type I) generated through electron abstraction or transfer from a substrate molecule and highly reactive state of oxygen known as singlet oxygen (Type II).

PDT is a multi-stage process. First a photosensitizer with negligible dark toxicity is administered, either systemically or topically, in the absence of light. When a sufficient amount of photosensitizer has accumulated in the diseased tissue, the photosensitizer is activated by exposure to light for a specified period. The light dose supplies sufficient energy to stimulate the photosensitizer, but not enough to damage neighboring healthy tissue. The reactive oxygen kills the target cells. Photodynamic therapy can be used to treat a variety of different diseases or conditions. However, a disease of particular interest for treatment using the photodynamic virus particles described herein is cancer.

Plant virus particles including photosensitizing agents can be used to treat cancer using photodynamic therapy. "Cancer" refers to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancer that can be treated using photodynamic therapy include head and neck cancer, skin cancer, cervical cancer, lung cancer, gastric cancer, prostate cancer, and breast cancer.

In some embodiments, the cancer being treated using the photodynamic virus particles of the present invention is skin cancer. Skin cancer is cancer that is found in the skin. The three main types of skin cancer include basal-cell skin cancer, squamous-cell skin cancer and melanoma. Other types of skin cancer include dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, and angiosarcoma. There are a variety of different symptoms associated with skin cancer. These include changes in the skin that do not heal, ulcering in the skin, discolored skin, and changes in existing moles, such as jagged edges to the mole and enlargement of the mole. The three main types of skin cancer can be distinguished by visual inspection of the cancer.

In some embodiments, the cancer being treated using the photodynamic virus particles of the present invention is melanoma. Melanoma is a type of cancer that develops from the pigment-containing cells known as melanocytes. Melanoma typically develops in the skin, but can also occur in the mouth, intestine, or eye. Early signs of melanoma are changes to the shape or color of existing moles or, in the case of nodular melanoma, the appearance of a new lump anywhere on the skin. At later stages, the mole may itch, ulcerate or bleed. Early signs of melanoma are summarized by the mnemonic "ABCDE," which refers to asymmetry, borders (irregular with edges and corners), color (variegated), diameter (greater than 6 mm), and evolving over time.

The photodynamic virus particles can be used to target cancer in a subject. As used herein, targeting cancer tissue includes the ability of the photodynamic virus particles to reach and preferably accumulate in a tumor after being administered to the subject. The ability of plant virus particles to target cancer tissue is supported by the biodistribution studies carried out by the inventors. See International Patent Publication WO/2013/181557, the disclosure of which is incorporated herein by reference. While not intending to be bound by theory, it currently appears that plant virus particles are drawn to the leaky vasculature caused by the angiogenesis associated with rapid tumor growth, and this leaky vasculature encourages entry for nanoparticles through small pores, thereby delivering the photodynamic virus particles to the tumor cells. In addition, in some embodiments, the photodynamic virus particles are directed to tumor-associated macrophages, such as M2 macrophages. As a result of this preferential accumulation, embodiments of the invention can deliver about 10%, about 20%, about 30%, about 40%, or even about 50% or more of the injected dose to tumor tissue.

In some embodiments, the method further includes the step of treating the subject with an additional type of anticancer therapy. Additional methods of anticancer therapy include one or more methods selected from the group consisting of surgery (e.g., Mohs' micrographic surgery), cryoablation, thermal ablation, radiotherapy (e.g., external beam radiotherapy), chemotherapy, radiofrequency ablation, electroporation, alcohol ablation, high intensity focused ultrasound, photodynamic therapy, administration of monoclonal antibodies, and administration of immunotoxins. For treatment of melanoma, effective examples of cancer ablation include Treatments that are particularly effective for metastatic melanoma include the use of biologic immunotherapy agents ipilimumab, pembrolizumab, and nivolumab; BRAF inhibitors, such as vemurafenib and dabrafenib; and treatment with the MEK inhibitor trametinib.

Targeting Moieties

In some embodiments, a targeting moiety can also be attached to the photodynamic virus particle. By "targeting moiety" herein is meant a functional group which serves to target or direct the virus particle to a particular location, cell type, diseased tissue, or association. In general, the targeting moiety is directed against a target molecule. Thus, for example, antibodies, cell surface receptor ligands and hormones, lipids, sugars and dextrans, alcohols, bile acids, fatty acids, amino acids, peptides and nucleic acids may all be attached to localize or target the photodynamic virus particle to a particular site. In some embodiments, the targeting moiety allows targeting of the plant virus particles of the invention to a particular tissue or the surface of a cell. Preferably, the targeting moiety is linked to the exterior surface of the virus to provide easier access to the target molecule. Targeting ligands used to delivery of photodynamic virus particles to cancer cells include ligands specific for bombesin, folic acid, vimentin, and polyarginine cell penetrating peptides.

In some embodiments, the targeting moiety is a peptide. In further embodiments, the targeting moiety is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. The targeting antibody is directed against a cell-surface marker on a cancer cell; that is, the target molecule is a cell surface molecule. As is known in the art, there are a wide variety of cell surface molecules known to be differentially expressed on tumor cells.

Virus Particle Coatings

In some embodiments, a coating can be added to the exterior of the plant virus particle to improve bioavailability. Administering plant virus particles to a subject can sometimes generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the photodynamic virus particles is typically undesirable. Accordingly, in some embodiments it may be preferable to modify the exterior of the plant virus particle or take other steps to decrease the immune response. For example, an immunosuppressant compound can be administered to decrease the immune response. More preferably, the photodynamic virus particle can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the photodynamic virus particle is decreased by PEGylation. PEGylation is the process of covalent attachment of polyethylene glycol (PEG) polymer chains to a molecule such as a plant virus particle. PEGylation can be achieved by incubation of a reactive derivative of PEG with the plant virus particle exterior. The covalent attachment of PEG to the photodynamic virus particle can "mask" the agent from the host's immune system, and reduce production of antibodies against the carrier. PEGylation also may provide other benefits. PEGylation can be used to vary the circulation time of the filamentous plant virus carrier. For example, use of PEG 5,000 can provide an a photodynamic virus particle with a circulation half-life of about 12.5 minutes, while use of PEG 20,000 can provide a photodynamic virus particle with a circulation half life of about 110 minutes.

The first step of PEGylation is providing suitable functionalization of the PEG polymer at one or both terminal positions of the polymer. The chemically active or activated derivatives of the PEG polymer are prepared to attach the PEG to the photodynamic virus particle. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

Administration and Formulation of Photodynamic Virus Particles

In some embodiments, the photodynamic virus particle is administered together with a pharmaceutically acceptable carrier to provide a pharmaceutical formulation. Preferably, the pharmaceutically acceptable carrier is suitable for topical application of the photodynamic virus particles. However, in some cases, alternate formulations may be used when the cancer being treated is surgically exposed prior to photodynamic therapy. Pharmaceutically acceptable carriers enable the photodynamic virus particle to be delivered to the subject in an effective manner while minimizing side effects, and can include a variety of diluents or excipients known to those of ordinary skill in the art.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The photodynamic virus particles are preferably applied as part of a topical formulation. Topical administration of the photodynamic virus particles can be accomplished using various different formulations such as powders, sprays, ointments, pastes, creams, lotions, gels, solutions, or patches. The photodynamic virus particle may be mixed under sterile conditions with a pharmaceutically acceptable carrier, and with any preservatives, buffers, or propellants which may be required. The ointments, pastes, creams, solutions, foams, lacquers, oils and gels may contain excipients in addition to the photodynamic virus particle. An example of a suitable formulation for topical delivery of a photodynamic virus particle is a 70% ethanol and 30% propylene glycol solution.

Examples of topical formulations include ointments and creams. Ointments are homogeneous, semi-solid preparations intended for external application to the skin or mucous membranes. They are used as emollients or for the application of active ingredients to the skin for protective, therapeutic, or prophylactic purposes and where a degree of occlusion is desired. Ointments can be formulated using hydrophobic, hydrophilic, or water-emulsifying bases to provide preparations for various applications. Creams, on the other hand, are semi-solid emulsions; i.e., a mixture of oil and water. They are divided into two types: oil-in-water creams which are composed of small droplets of oil dispersed in a continuous aqueous phase, and water-in-oil creams which are composed of small droplets of water dispersed in a continuous oily phase.

The dosage amount and preferred type of formulation can be readily established by reference to known treatment or prevention regimens. The amount of photodynamic virus particle that is administered and the dosage regimen for treating a disease condition with a photodynamic virus particle using the method of this invention depends on a variety of factors, including the age, weight, sex, and medical condition of the subject, the severity of the disease, the site and frequency of administration, the character of the skin to which the agent is applied, and the particular compound employed, and thus may vary widely. Such treatments may be administered as often as necessary and for the period of time judged necessary by the treating physician. One of skill in the art will appreciate that the dosage regime or therapeutically effective amount of the inhibitor to be administrated may need to be optimized for each individual. The topical formulations may contain active ingredient in the range of about 0.001 to 10 mg/ml, preferably in the range of about 0.001 to 1 mg/ml and most preferably between about 0.01 and 0.1 mg/ml. Suitable amounts vary depending on the photodynamic virus particles being used, but can be readily determined by one skilled in the art.

Useful dosages of the photosensitizing agents and photodynamic virus particles can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the photodynamic virus particles vary depending upon many different factors, including means of administration, target site, physiological state of the patient, whether the patient is human or an animal, other medications administered, and whether treatment is prophylactic or therapeutic.

The present invention is illustrated by the following examples. It is to be understood that the particular examples, materials, amounts, and procedures are to be interpreted broadly in accordance with the scope and spirit of the invention as set forth herein.

EXAMPLES

Example 1

Utilizing Viral Nanoparticle/Dendron Hybrid Conjugates in Photodynamic Therapy for Dual Delivery to Macrophages and Cancer Cells The present example demonstrates the therapeutic efficacy of nanoparticle delivery of a photosensitizer (PS) for the treatment of melanoma, a highly resistant and aggressive cancer where photodynamic therapy (PDT) could be applied for greater treatment efficiency. In the process, the inventors have established CPMV/dendron hybrids as a platform for expanding particle modification and drug loading capabilities, and also examined the macrophage specificity of CPMV for potential selective delivery. Specifically, the incorporation of PS into a CPMV-based nanoparticle using electrostatic interactions with anionic generation 3 carboxyl dendrons present on CPMV was examined. Notably, these dendron polymers possess 8 carboxyl groups branching out from a single focal point, which were utilized to enhance the negative charge of the capsid for improved association with the positively charged PS. However, the dendrons also result in an increase in the number of reactive groups displayed on the surface, which could be employed for other applications, such as the attachment of targeting ligands or imaging agents.

The results with the PS-CPMV conjugate demonstrate a significant improvement in the effective elimination of both macrophage and tumor cells when compared to just the photosensitizer itself, which suggests a wider role for this type of conjugation strategy for improved PDT treatment of cancer.

RESULTS AND DISCUSSION

Design of CPMV-Based Photosensitizer

CPMV was first modified with carboxyl dendrons to impart a greater negative charge, but also with the potential for enhanced functionalizability. CPMV has a highly symmetric structure that is known to atomic scale resolution, and strategies for both interior and exterior chemical conjugation have been established. Wen et al., Biomacromolecules, 13, 3990-4001 (2012); Wang et al., Chem Biol., 9, 805-811 (2002). There are 300 lysines displayed in precisely defined arrays on the surface of CPMV that can be targeted. The reaction scheme is shown in FIG. 1*a*. Azide groups were first attached to CPMV using N-hydroxysuccinimide (NHS) ester chemistry to target the lysine residues. Following linker attachment, copper(I)-catalyzed azide-alkyne cycloaddition was used to conjugate an alkyne-functionalized generation 3 dendron with carboxyl groups to the azide-modified CPMV to form a CPMV/dendron hybrid (CPMV*). After dendron attachment, the carboxyl groups now displayed on CPMV were allowed to associate with the cationic Zn-EpPor PS through electrostatic interactions (FIG. 1*b*). Unbound PS was removed by ultracentrifugation, leaving CPMV decorated with PS (PS-CPMV*). Unmodified CPMV was also incubated with PS to compare differences in binding affinity due to the increased charge density.

Characterization of the particles was performed by agarose and SDS gel electrophoresis, transmission electron microscopy (TEM), and UV/visible spectroscopy (FIG. 2). Using a native agarose gel, it was observed that conjugation of NHS-azide and carboxyl dendrons both resulted in increased mobility down the gel, as expected. The attachment of the azide to lysine groups on CPMV would result in negation of the positively charged amino acid and faster migration toward the anode. A similar effect was seen for CPMV* due to the negative charge of the carboxyl groups displayed on the dendrons. Additional analysis of carboxyl dendron attachment using an SDS denaturing gel showed successful modification of the coat proteins of CPMV, with additional densities appearing above the unmodified coat protein bands. Density measurements using ImageJ analysis revealed ~45% modification, or 135 out of 300 possible lysines modified and 1080 carboxyl groups introduced from the 8-arm dendrons. Assessment of the particles by TEM showed that the particles remained intact during modification. After utilizing the carboxyl groups for PS incorporation, UV/visible spectroscopy revealed about 200 PS bound to the CPMV* particles compared to 100 per unmodified CPMV. The CPMV capsid has a negative zeta potential, which contributes to the interaction of PS with the wild-type particle. However, the additional negative charge imparted by the dendrons was able to double the PS loading capacity of CPMV. Through visual examination, an advantage of the nanocarrier observed was that the particles remained well dispersed when stored in the fridge over a period of a month, whereas in the same time frame the free PS solution displayed aggregation and sedimentation.

Figure 3:
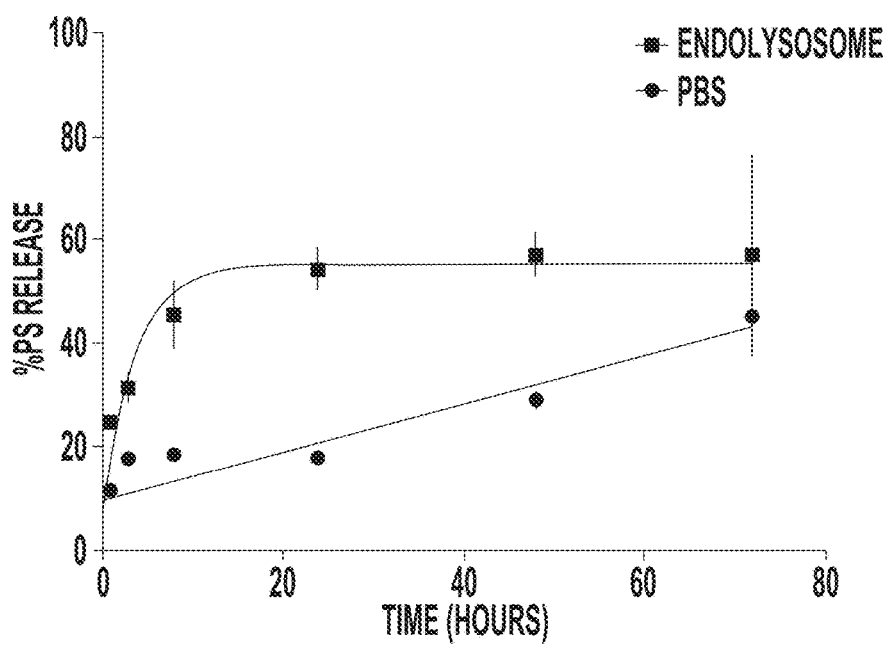
FIG. 3 provides a graph of the PS release profile. PS-CPMV* was dialyzed against PBS and endolysosomal buffer (pH 5) at 37° C. using dialysis units with a molecular weight cutoff of 10 kDa. Samples at each time point were analyzed by UV/visible spectroscopy to determine PS concentration. The measurements were performed in triplicate.

The stability of PS-CPMV* was investigated, with incubation in various solutions explored. The particles were diluted to a concentration of 1 mg/mL and dialyzed against 45 mL of PBS (pH 7) and endolysosomal buffer (pH 5) over a period of 3 days at 37° C. (FIG. 3). The endolysosomal buffer was prepared by combining 200 mM citric acid and 200 mM dibasic sodium phosphate buffers such that the final pH was representative of the lysosomal compartment. A slow, almost linear release of PS was observed in PBS buffer, not quite reaching 50% release even after 3 days. On the other hand, a burst release of PS was observed after incubation in the endolysosomal buffer, and 50% release was achieved by around 10 h. The quicker dissociation of PS in the endolysosomal buffer compared to PBS can be attributed to the low pH condition, leading to protonation of the carboxylates and release of the electrostatically coupled PS. Overall, these results are positive, indicating that PS-CPMV* is stable at physiological pH and that low pH can be used to trigger efficient PS dissociation.

Photodynamic Therapy of Macrophages

Figure 4A:
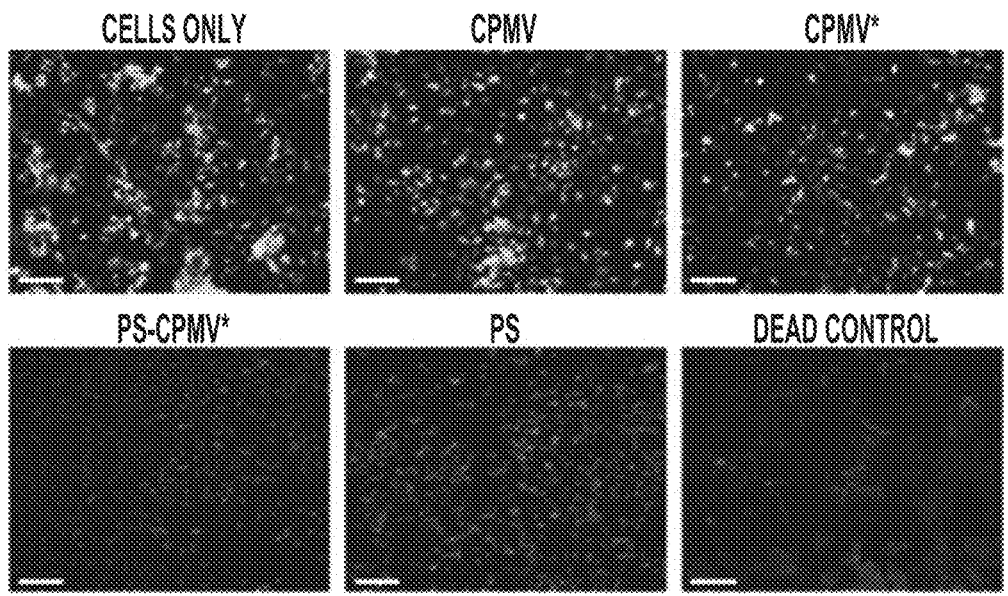
FIGS. 4A-4C provide graphs and images showing the results of a LIVE/DEAD assay of RAW 264.7 macrophages. (a) Representative images after photodynamic therapy of cells incubated with CPMV, CPMV*, PS-CPMV*, or PS and LIVE/DEAD cell staining. Incubation for 30 min with 70% methanol was utilized as a control for dead cells. Calcein-AM staining of live cells is shown in green, and ethidium homodimer-1 staining of dead cells is shown in red. Scale bar=200 µm. (b) Dark controls show no cytotoxicity of CPMV formulations or PS alone in the absence of light therapy. Scale bar=200 µm. (c) Quantification of percentage live cells as measured by ImageJ analysis. Two images for each sample in triplicate were analyzed, and error bars show the standard deviation.
Figure 4B:
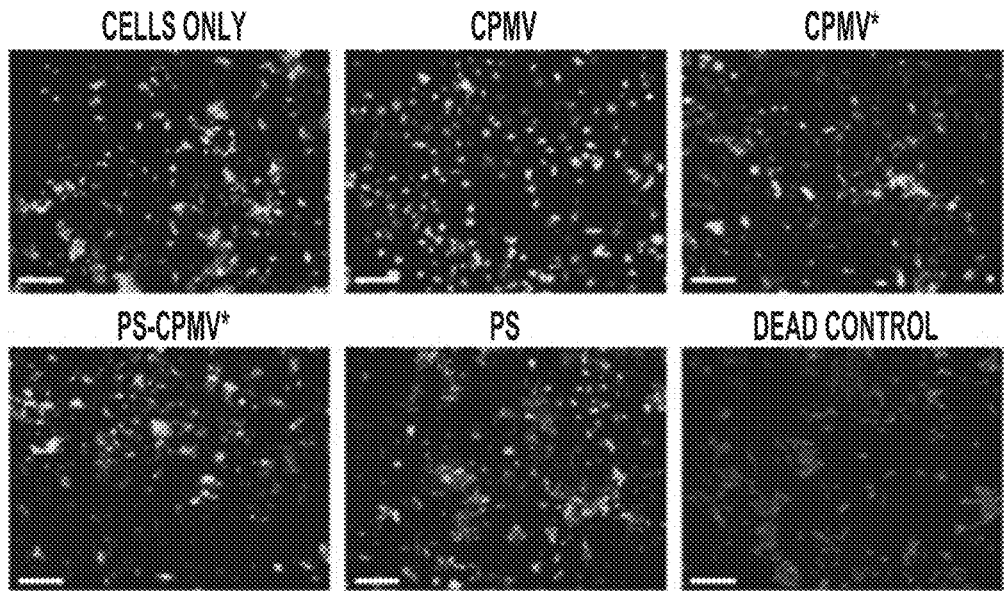
Figure 4C:
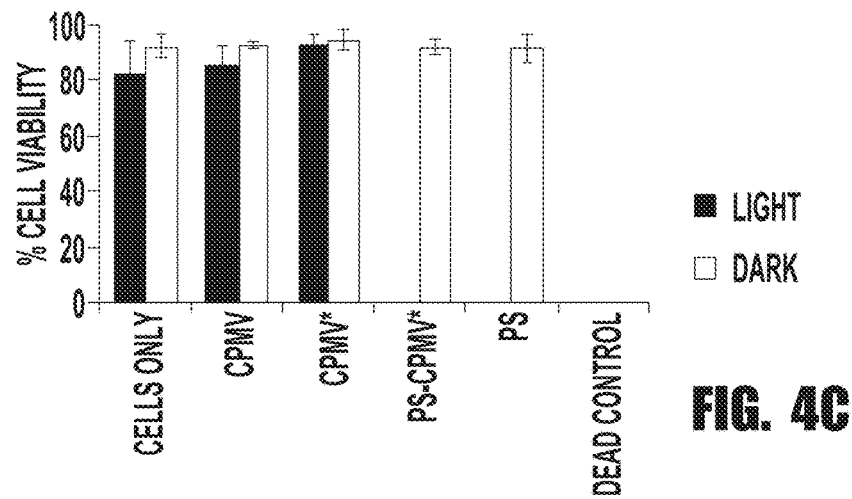

Uptake of PS-CPMV* and its efficacy for PDT of RAW 264.7 murine macrophages was initially tested using a LIVE/DEAD cell viability assay in a 96-well plate. The macrophages were allowed 8 h to take up either PS-CPMV* at a concentration of 5.0 µM PS or CPMV, CPMV*, and PS controls normalized according to PS or CPMV concentration. After washing, PDT was initialized using a mirror setup where light from a projector was reflected on the cell plate for 30 min. Cells were incubated overnight, then stained with a combination of calcein-AM and ethidium homodimer-1 to detect live and dead cells, respectively (FIG. 4a). While cytotoxicity was not observed with the dark controls (FIG. 4b), PS-CPMV* and PS were effective at completely eliminating the macrophages, which is quantified in FIG. 4c.

There is a possibility that the macrophage subpopulations have differences in proteolytic processing and cleavage of the Alexa Fluor 488 from the dye-labeled CPMV, resulting in brighter signal in the M2 subpopulation that was not observe when using dye-labeled antibodies. There may also be differences in the polarization states between the experiments. To address these issues, additional inclusion of IFN-γ for greater stimulation of M1 polarization and flow cytometry measurements based on PS signal were also investigated. One marker for differentiating macrophage phenotype is their metabolism of arginine. M1 macrophages use nitric oxide synthase (iNOS) to metabolize arginine to citrulline and nitric oxide, while M2 macrophages use arginase-1 (Arg1) for the production of urea, polyamines, and ornithine. Polarization of the macrophages was confirmed using reverse transcription polymerase chain reaction (RT-PCR) to detect relative expression levels of the two genes. RNA was extracted from the stimulated and unstimulated cells, cDNA synthesized, then iNOS- and Arg1-specific primers used for PCR (FIG. 5b). There were clear differences in the expression levels of iNOS and Arg1, with higher expression of iNOS for the LPS- and IFN-γ-treated cells and Arg1 expression only observed for cells stimulated with IL-4.

Flow cytometry was again performed using a similar setup as above, except modified to evaluate PS signal in the macrophages rather than using antibody staining (FIG. 5c). There was a difference in the fluorescence intensity of the M1 and M2 cells only controls, which was not observed for the first flow cytometry study. The disparity between the two experiments is likely due to differences in the excitation wavelength, since the secondary antibody for CPMV staining is excited at 651 nm and PS is excited at 440 nm. The PS signal was higher in the M1 subpopulation, both for the cells only control and for cells incubated with PS-CPMV*. Due to differences in the background fluorescence, although overall the mean fluorescence intensity was greater for M1 cells, the relative shift in fluorescence was around 325 for both subpopulations, so there is some ambiguity as to whether PS-CPMV* association was greater for the M1 subpopulation. Nevertheless, the M2 phenotype was clearly not favored, corroborating data obtained based on the signal from detection of CPMV.

Based on the above results, it is likely that factors other than dye release or insufficient polarization are contributing to the differences observed between the previous and current studies in regard to the affinity of the cells to the PS particles, which will be the subject of further study. For applications in PDT, CPMV specificity for M2 macrophages would be preferable for combination therapy of tumor cells and immunosuppressive macrophages. However, specificity for M1 macrophages could also be utilized for delivery of stimulatory factors that prevent their phenotype switching as well as for aiding in their recruitment of immune cells. The CPMV platform has the additional advantage in terms of immunotherapy due to the fact that it has recently been shown to induce potent antitumor immune response after in situ vaccination in models of skin, ovarian, breast, and colon cancers due to association with and activation of neutrophils. Lizotte et al., Nat Nanotechnol., 11, 295 (2015). Enhanced efficacy may then be observed from PDT together with the immunostimulatory effect of CPMV.

Photodynamic Therapy of Melanoma

To confirm PDT activity, we evaluated the efficacy of the PS-CPMV* conjugate using the highly aggressive B16F10 melanoma cell line. Uptake of the particles and delivery of PS was first studied using confocal microscopy. B16F10 cells were incubated with PS-CPMV* particles for 3 h, fixed, and stained for the nuclei using 4',6-diamidino-2-phenylindole (DAPI) and cell membranes using wheat germ agglutinin (WGA). Based on fluorescence signal from the porphyrin, confocal imaging showed that the drug was indeed taken up by the melanoma cells (FIG. 6a). Although CPMV is known to be taken up by endocytosis and distributed in punctate patterns throughout the cytoplasm (Plummer E M, Manchester M., Mol Pharmaceutics. 10, 26-32 (2013)), the signal from PS was found to be distributed throughout the cell, including within the nucleus, indicating that the drug gets released from the particles (see FIG. 3) and escapes from the endolysosomes.

The distribution of PS throughout the cell is advantageous for PDT. Efficacy was examined using white light therapy of B16F10 cells incubated with CPMV, CPMV*, or PS-CPMV* for 8 h, with concentrations of PS ranging from 0.025 to 5 µM tested. After removal of unbound or noninternalized drug, cell killing was achieved using white light therapy for 30 min, and cell viability was measured using an MTT cell viability assay to assess cell metabolic activity (FIG. 6b). A 2-fold improvement in efficacy was achieved with PS-CPMV* when compared to free PS, with an IC50 of 0.28 µM calculated for PS-CPMV* compared to 0.54 µM for PS alone. Toxicity was not observed for cells incubated with CPMV or CPMV* tested at the highest CPMV concentration used for PS-CPMV*, and the dark controls also remained unaffected. The low µM IC50 of PS-CPMV* is highly effective for PDT and on par with other photosensitizers being evaluated. Rangasamy et al., J Med Chem. 58, 6864-6874 (2015); Tachikawa et al., Bioorg Med Chem., 22, 4745-4751 (2014). The difference in efficacy between PS and PS-CPMV* could be attributed to more efficient cellular delivery with the nanoparticle.

The advantage of using a nanocarrier is expected to be more profound when applied in vivo, where the nanoparticle would be better able to transport the drug. There have been a number of prior studies that illustrate the well-suited in vivo performance of CPMV. For example, mouse studies have indicated high biocompatibility, as no toxicity was observed even at doses up to 100 mg/kg body weight. Singh et al., J Controlled Release., 120, 41-50 (2007). Investigations of biodistribution demonstrate standard nanoparticle clearance behavior through mainly the liver and spleen, and quick clearance from tissues was observed only after a few days. Additionally, functionalization of CPMV for delivery to cancer cells has been demonstrated with targeting ligands such as bombesin, folic acid, and polyarginine cell penetrating peptides. Therefore, not only does the CPMV platform offer a better solubility profile for PS transport, it also presents the prospect of multimodal formulations that incorporate active targeting for cell-specific delivery.

CONCLUSIONS

This work has shown that CPMV/dendron hybrids can be beneficial for introducing greater functionality to the particles. The use of carboxyl dendrons for the increased incorporation of cationic photosensitizers was demonstrated, but the use of dendrons can be applied for a range of other applications, such as enhancement of contrast agent loading and amplification of targeting ligand density. Delivery of the photosensitizer to macrophages was shown to be effective for their elimination. While the inventors were not able to reproduce the previously reported preference of CPMV for the M2 macrophage subpopulation, there were differences in uptake between the M1 and M2 populations observed, and further investigation is warranted. Specificity in targeting one the two subpopulations would be of interest for tuning the delivery of agents to achieve either enhancement of immunostimulatory or elimination of immunosuppressive effects. Overall, PS-CPMV* was found to be effective for PDT of B16F10 melanoma cells, aiding in the delivery of PS. The high efficacy of the Zn-EpPor PS, with an IC50 in the low µM range, makes it an attractive candidate for cancer therapy, but the hydrophobicity of the photosensitizer would likely detract from its application in vivo. Using a nanocarrier would be advantageous for reducing undesirable side effects, and the potential for synthesizing a targeted formulation would be a further benefit for carrying this technology forward.

EXPERIMENTAL PROCEDURES

Dendron and Photosensitizer Synthesis

Carboxyl dendrons were synthesized through a ring-opening reaction between succinic anhydride (200 mg, 2.0 mmol) in 5 mL of dried tetrahydrofuran (THF) and a generation 3 polyester-8-hydroxyl-1-acetylene bis-MPA dendron (Sigma, 86.8 mg, 0.1 mmol) in the presence of triethylamine (TEA, 167 mL, 1.2 mmol) and 4-dimethylaminopyridine (DMAP, 48.9 mg, 0.4 mmol) that were dissolved in 10 mL of dried THF. The reaction was stirred for 24 h at 40° C., the solvent evaporated, and methanol added to dissolve the mixture. The final product was purified by dialysis against methanol using dialysis tubing with a molecular weight cutoff of 100-500 Da. Verification of the product was performed by $^1$H NMR analysis.

The cationic zinc ethynylphenyl porphyrin photosensitizer (Zn-EpPor PS) used in this study was synthesized based on previously published methods. Feese et al., Biomacromolecules, 12, 3528-3539 (2011). In brief, the porphyrin was first synthesized under mildly acidic conditions using 4-pyrindinecarboxaldehyde, 4-[(trimethylsilyl)ethynyl]-benzaldehyde, and pyrrole then purified by column chromatography. Ethyne deprotection was accomplished in a 1:4 solution of methanol/THF with potassium carbonate, then zinc acetate in methanol/THF was used for addition of zinc. Finally, iodomethane in dimethylformamide (DMF) at elevated temperatures was used for amine quaternization of the pyridine substituents.

CPMV Purification

CPMV was propagated in *Vigna unguiculata* black-eyed pea plants 10-14 days after planting using mechanical inoculation with a 0.1 mg/mL solution of CPMV. Viral particles were isolated using a combination of blending, chloroform/butanol extraction, and centrifugation based on established methods. Cho et al., Methods Mol Biol., 1108, 211-230 (2014).

CPMV Modifications

CPMV was first modified with azide linkers using an overnight reaction of 6000 molar excess of N-hydroxysuccinimide (NHS)-PEG$_4$-azide (Thermo Scientific) with a 2 mg/mL concentration of CPMV in 0.1 M potassium phosphate (KP) buffer, pH 7.0 with 10% (v/v) DMSO. Purification was performed by ultracentrifugation pelleting at 42,000 rpm. To further display carboxyl dendrons on CPMV (CPMV*), alkyne-functionalized carboxyl dendrons were attached using 2400 molar excess with 2 mg/mL CPMV-N$_3$ in 0.1 M KP buffer, pH 7.0 in the presence of 20 mM aminoguanidine, 20 mM 1-ascorbic acid, and 2 mM CuSO$_4$ that was added together with 10 mM tris(benzyltriazolylmethyl)-amine (THPTA). 10 kDa molecular weight cutoff centrifugal filters (Millipore) were used to purify the reaction after 2 h at room temperature. Drug-labeled formulations were then made by incubating 1000 molar excess of PS (from 50 mg/mL stock) with CPMV* in 10 mM KP buffer, pH 7.8 overnight, then removing unattached PS by ultracentrifugation pelleting in 0.1 M KP buffer, pH 7.8, which was also the buffer used for resuspension of the particles. Any aggregates were removed by a clearing spin at 10,000 rpm for 10 min before obtaining the final solution.

UV/Visible Spectroscopy

CPMV and PS concentrations were determined by UV/visible spectroscopy, with a molar absorptivity coefficient for CPMV of 8.1 $mg^{-1}$ mL $cm^{-1}$ at 260 nm and for PS of 195 000 $M^{-1}$ $cm^{-1}$ at 440 nm.

Gel Electrophoresis

DNA samples were analyzed with 2% (w/v) agarose gels run in TAE buffer at 100 V for 1 h and stained with GelRed nucleic acid stain (Biotium). CPMV samples were analyzed by agarose gel electrophoresis with 1.2% (w/v) agarose gels run in TBE buffer at 100 V for 1 h. CPMV particles were also denatured into individual coat protein subunits by heating for 5 min at 100° C., then separated on denaturing 4-12% NuPAGE gels (Invitrogen) in MOPS running buffer (Invitrogen). CPMV gels were stained using Coomassie blue, and all gels were photographed using an AlphaImager imaging system (Biosciences).

Transmission Electron Microscopy

Particles were diluted in distilled water and adsorbed to Formvar carbon-coated copper grids at a concentration of 0.1 mg/mL for 5 min. This was followed by a brief wash with distilled water, then negative staining with 2% (w/v) uranyl acetate for 2 min. Imaging was performed using a Zeiss Libra 200FE transmission electron microscope at 200 kV.

LIVE/DEAD Assay

RAW 264.7 macrophages were seeded overnight in 96-well plates, with one plate used as a dark control, at a concentration of 10,000 cells/100 µL Dulbecco's modified Eagle's medium (DMEM, Gibco) supplemented with 10% (v/v) fetal bovine serum (FBS, Atlanta Biologicals) and 1% (v/v) penicillin-streptomycin (pen-strep, Life Technologies). Cells were then incubated for 8 h at 37° C. and 5% $CO_2$ with triplicates of CPMV, CPMV*, PS-CPMV*, or PS corresponding to 5.0 µM PS or normalized for nanoparticle concentration accordingly. After washing twice with PBS, 100 µL medium was added. Photodynamic therapy was applied using a Vivitek D950HD projector reflected off a mirror to result in a rectangular area (10.5 cm×11 cm) that corresponded to a dose of about 18.1 J $cm^{-2}$ at 430 nm, and then the cells were returned to the incubator overnight. Treatment with 70% (v/v) methanol for 30 min was used as a control for dead cells. Cell viability was determined using a LIVE/DEAD assay for mammalian cells (Thermo Fisher) following manufacturer's procedures for cell staining and using a Zeiss Axio Observer Z1 motorized FL inverted microscope for imaging. Analysis was performed with ImageJ to measure percentage cell viability.

Macrophage Cell Polarization

RAW 264.7 macrophages were seeded in 6-well plates at a concentration of 500,000 cells/2 mL DMEM supplemented with 10% (v/v) heat-inactivated FBS and 1% (v/v) pen-strep. After 5 h for growth and adhesion at 37° C. and 5% $CO_2$, 50 ng/mL of either LPS (Sigma) or IL-4 (Biolegend) was added to the wells for M1 and M2 polarization, respectively, and allowed to stimulate the cells for an additional 24 h. As an additional method for M1 polarization, 50 ng/mL of LPS and 20 ng/mL of IFN-γ (Biolegend) was also evaluated.

Reverse Transcription Polymerase Chain Reaction (RT-PCR)

RNA extraction was carried out using TRI Reagent (Molecular Research Center) according to manufacturer's specifications. cDNA was made using SuperScript VILO Master Mix (Invitrogen) with 500 ng of RNA. DreamTaq PCR Master Mix (Thermo Scientific) was then used to analyze gene expression of iNOS, arginase-1 (Arg1), and β-actin. See Hou et al., Int J Mol Med., 32, 503-510 (2013). Amplification was performed with 2 µL of cDNA diluted 1:10 and 4 pmol of each primer in a 20 µL reaction with the following steps: (1) 2 min at 94° C.; (2) 30 cycles of 94° C. for 30 s, 55° C. for 20 s, 72° C. for 20 s; and (3) 5 min at 72° C. for final extension. Expected product sizes were 372 bp for iNOS, 249 bp for Arg1, and 154 bp for β-actin.

Flow Cytometry

After macrophage polarization (see above), the cells were removed with Hanks'-based cell dissociation buffer (Gibco) and resuspended in sterile PBS. The cells were added to v-bottom 96-well plates at a density of 300 000 cells/200 µL (for PS signal) or 500,000 cells/200 µL (for CPMV antibody staining) and incubated with 100,000 particles/cell for 3 h at 37° C. The cells were washed twice with FACS buffer (PBS with 1 mM EDTA, 25 mM HEPES, 1% (v/v) FBS, pH 7.0), fixed with 2% (v/v) formaldehyde in FACS buffer for 10 min at room temperature, then washed twice again with FACS buffer. Data obtained based on PS signal were acquired using a BD FACSAria SORP cell sorter gated for 10,000 events. CPMV staining was performed by first briefly permeabilizing the membrane with permeabilization buffer (0.2% saponin in FACS buffer). The cells were incubated at 4° C. for 1 h with primary rabbit anti-CPMV antibody (Pacific Immunology) diluted 1:1000 in permeabilization buffer, washed twice with permeabilization buffer, incubated another hour at 4° C. with Alexa Fluor 647-labeled goat anti-rabbit secondary antibody (Thermo Scientific) diluted 1:2000 in permeabilization buffer, and then washed three times with permeabilization buffer. After the final wash, the cells were resuspended in FACS buffer and analyzed on a BD LSR II flow cytometer, gated for 10 000 events. Data were processed using FlowJo software (Tree Star).

PS Release Assay

To study PS release, PS-CPMV* was incubated in PBS and endolysosomal buffer (28 mL of 200 mM citric acid mixed with 65.5 mL of 200 mM dibasic sodium phosphate, pH 5). Jordans et al., BMC Biochem., 10, 23 (2009). 200 µL of 1 mg/mL PS-CPMV* was dialyzed using a Slide-A-Lyzer Mini dialysis unit (10 kDa molecular weight cutoff) in 45 mL of each solution prewarmed to 37° C. Samples were incubated at 37° C. with shaking (80 rpm). 10 µL of the samples was removed at 1, 3, 8, 24, 48, and 72 h, and the concentration of PS remaining was determined by UV/visible spectroscopy (see above). Analysis was performed using GraphPad Prism.

Confocal Microscopy

Localization of PS after cell uptake of PS-CPMV* in B16F10 melanoma cells was evaluated by confocal microscopy. Cells were seeded on coverslips in untreated 24-well plates at a concentration of 25,000 cells/500 µL DMEM supplemented with 10% (v/v) FBS and 1% (v/v) pen-strep and allowed to grow overnight at 37° C. and 5% $CO_2$. All steps following were performed in the dark. PS-CPMV* was added at a concentration of $1 \times 10^7$ particles/cell, and then the cells were returned to the incubator for 3 h. Cells were fixed using DPBS containing 4% (v/v) paraformaldehyde and 0.3% (v/v) gluteraldehyde for 10 min at room temperature. After washing 3 times with DPBS, the cells were incubated with 1 µg/mL Alexa Fluor 488-conjugated wheat germ agglutinin (Invitrogen) in DPBS with 5% (v/v) goat serum for 45 min at room temperature. The cells were washed a further 3 times with DPBS, and then the coverslips were mounted onto microscope slides with Fluoroshield with DAPI (Sigma). Imaging was performed using an Olympus FluoView FV1000 confocal microscope and analysis performed with ImageJ.

MTT Cell Viability Assay

B16F10 cells were seeded (2000 cells/100 µL DMEM/well) in a treated 96-well plate overnight at 37° C. and 5% $CO_2$. Triplicates of PS-CPMV* were added to the cells at concentrations of 0.025, 0.05, 0.1, 0.25, 0.5, 1.0, and 5.0 µM PS. CPMV and CPMV* matching the CPMV concentration for PS-CPMV* at 5.0 µM PS were used as controls, along with cells with no added particles. A dark control for all the samples was also used. The cells were incubated at 37° C. and 5% $CO_2$ for 8 h to allow for cell binding and uptake. Free particles and PS were washed with PBS and 100 µL of fresh medium added. The cells were then irradiated with white light for 30 min as detailed above with the LIVE/DEAD assay. The cells were returned to the incubator for 48 h after treatment, and their viability was subsequently measured using an MTT cell proliferation assay kit (ATCC) based on manufacturer's instructions. A Tecan Infinite 200 plate reader was used to measure absorbance at 570 nm, and the percent cell viability was determined by normalizing to the cells only control. Data analysis was performed with GraphPad Prism.

Example II

A TMV-Based Photosensitizer for Imaging and Treatment of Aggressive Melanoma Toward the goal of developing a nanoparticle PDT technology, a biology-inspired platform was evaluated, specifically using the nanocarriers formed by plant viruses as the delivery system. Plant virus-based scaffolds can be produced inexpensively at high yields through molecular farming. The protein-based nanoparticles are highly monodisperse, and their structures are known to atomic resolution. Viruses have naturally evolved to deliver cargos, but plant viruses are non-infectious toward mammals. They are biocompatible and biodegradable, and therefore offer favorable properties for in vivo medical applications.

In this study, the inventors focused on the nucleoprotein components formed by the tobacco mosaic virus (TMV). TMV is a 300×18 nm hollow rod, with a 4 nm-wide interior channel. Its structure is known to atomic resolution and the chemistries for modifying the coat protein have been well established. The in vitro and in vivo properties of TMV have been well characterized: TMV exhibits shape-mediated enhanced tumor homing and penetration compared to spherical viruses. Bruckman et al., Virology 449, 163-73 (2014). Therefore, it was suspected that TMV would be a suitable carrier for delivery of photosensitizers. Specifically, the inventors sought to develop TMV as a carrier for a porphyrin-based photosensitizer: 5-(4-ethynylphenyl)-10, 15,20-tris-(4-methylpyridin-4-ium-1-yl)porphyrin-zinc(II) triiodide (Zn-EpPor). Feese et al., Biomacromolecules 12 (10), 3528-39 (2011).

Zn-EpPor is a cationic porphyrin (FIG. 7A) previously used in antimicrobial photodynamic inactivation (aPDI) studies. It has been successfully conjugated to cellulose, both as nanocrystals and as fibers, to create photoactivatable materials that were shown to be effective against various strains of drug resistant bacteria, including multidrug-resistant *Acinetobacter baumannii* (MDRAB), methicillin-resistant *Staphylococcus aureus* (MRSA), and vancomycin-resistant *Enterococcus faecium*, as well as effective against viruses, including dengue-1, influenza A, and human adenovirus-5. Carpenter et al., Biomacromolecules 16 (8), 2482-92 (2015). Unlike other porphyrin-based PDT molecules, Zn-EpPor has an overall cationic charge and contains a zinc molecule within the porphyrin ring. Recent work indicates that the presence of a cationic charge enhances accumulation within the mitochondria, while the presence of zinc stabilizes the porphyrin ring, both of which improve therapeutic efficacy. Pavani et al., Photochemical & photobiological sciences: Official journal of the European Photochemistry Association and the European Society for Photobiology, 8 (2), 233-40 (2009). Zn-EpPor is unique in that it contains both these characteristics, making it a suitable candidate for a proof-of-principle study using a nanoparticle strategy targeting cancer. The results demonstrate the nanoparticle-formulation of Zn-EpPor and its use in cancer PDT. Specifically, Zn-EpPor was encapsulated into the central TMV channel, allowing for increased therapeutic delivery and efficacy. As a proof-of-concept, melanoma was studied as the test bed.

Results and Discussion

$Zn$-$EpPor$TMV Encapsulation and Characterization

Tobacco mosaic virus (TMV) was produced in and purified from *Nicotiana benthamiana* plants as previously described. Bruckman, M. A.; Steinmetz, N. F., Methods in molecular biology, 1108, 173-85 (2014). The nucleoprotein components of TMV form a hollow cylinder measuring 300×18 nm with a 4 nm-wide interior channel. Each TMV particle is comprised of 2,130 identical copies of a coat protein, each containing two solvent-exposed glutamic acids (Glu97, Glu106) on the interior surface and a tyrosine residue (Tyr139) on the exterior (FIG. 7A). In this study, a lysine-added mutant was also considered (TMV$_{Lys}$, T158K) that also offers an amine ligation handle on the solvent-exposed exterior surface (FIG. 7A). Demir, M.; Stowell, M. H. B., Nanotechnology, 13 (4), 541-544 (2002). Two drug loading strategies were considered: 1) covalent conjugation of Zn-EpPor to the aforementioned amino acid side chains or non-covalent drug loading through electrostatic interactions.

The drug candidate, Zn-EpPor, was designed and synthesized with an alkyne handle (FIG. 7A) for covalent conjugation to an azide-bearing motif using the Cu(I)-catalyzed Huisgen-Meldal-Sharpless 1,3-dipolar cycloaddition reaction. In brief, TMV$_{Lys}$ was first modified with an azide functional handle using N-hydroxysuccinimide (NHS) ester-PEG$_4$-azide, followed by the click reaction using Zn-EpPor and reaction conditions as previously described. Bruckman et al., Chembiochem: a European journal of chemical biology, 9 (4), 519-23 (2008). However, any conjugation attempts resulted in extensive aggregation and loss of the sample, and therefore were not further pursued.

Instead, Zn-EpPor was loaded into TMV making use of the chemically distinct exterior and interior microenvironments. The interior channel of TMV is lined with a high density of negative charges from solvent-exposed glutamic acids Glu97 and Glu106 (FIG. 7A). It was hypothesized that the positively charged drug candidate Zn-EpPor carrying 3 positive charges, one at each of the methylpyridinium side chains, could be loaded into the central channel of TMV based on charge-charge interactions. Zn-EpPor loading was carried out under slightly alkaline condition (pH 7.8) to promote deprotonation of the carboxylic acids and therefore electrostatic complexation with Zn-EpPor (Zn-EpPor was used at a 6,000 fold molar excess to TMV). The reaction was allowed to proceed overnight, then excess Zn-EpPor was removed using ultracentrifugation (FIG. 7B). To confirm whether loading occurred and whether free Zn-EpPor was removed following centrifugation, $_{Zn-EpPor}$TMV was analyzed using size exclusion chromatography (FIG. 7D). TMV showed the characteristic elution profiles at 8 mL using the Superose6 column and ÄKTA purifier; broken particles or free coat proteins were not detectable. The co-elution of the 260 nm (RNA component) and 280 nm (protein component) and 440 nm (Zn-EpPor specific absorbance) peaks indicate successful loading into TMV. No additional peaks were observed at any of the wavelengths measured, indicating that $_{Zn-EpPor}$TMV was both intact and void of free Zn-EpPor.

The loading efficiency was quantified using UV/visible spectroscopy and inductively coupled plasma optical emission spectroscopy (ICP-OES) (FIG. 7E). Using the Beer-Lambert law and the TMV- and Zn-EpPor-specific molar absorptivity coefficients ($\varepsilon_{TMV}$=3.0 mgmL$^{-1}$ cm$^{-1}$ at 260 nm; $\varepsilon_{Zn-EpPor}$=195,000 M$^{-1}$ cm$^{-1}$ at 450 nm), the concentrations of TMV and Zn-EpPor in solution, and hence the ratio of Zn-EpPor:TMV, were determined. On average, 800 Zn-EpPor were loaded into a TMV particle. The UV/visible spectroscopic method was complemented with ICP-OES measurements to quantify the Zn loading. The latter method may be considered more accurate, because the porphyrin molar absorptivity coefficient is solvatochromic and may be different in the TMV microenvironment than in free solution. For ICP-OES, zinc was released from Zn-EpPorTMV by incubation at 60° C. for 2 hours in 1M HCl. Zinc content was then quantified based on a calibration standard curve. Overall, the data were in good agreement indicating loading of approximately 900±15% Zn-EpPor per TMV.

To confirm that Zn-EpPor was indeed loaded into the interior channel, and not non-specifically adsorbed on the exterior particle surface, TMV was modified on either the interior (TMV-iAlk) or exterior (TMV-eAlk) surface with alkyne groups to mask charged amino acids. In brief, alkyne handles were attached to either the interior or exterior surfaces of TMV using EDC chemistry to target interior glutamic acids or diazonium salt modification to target the exterior tyrosine residue, using previously established protocols. Bruckman, M. A.; Steinmetz, N. F., Methods in molecular biology, 1108, 173-85 (2014). Native TMV, TMV-iAlk, and TMV-eAlk were incubated with Zn-EpPor as described above. Following purification, Zn-EpPor loading was quantified using ICP-OES (FIG. 7C). Indeed, interior modification of glutamic acid residues with alkynes indicated a decreased loading efficiency resulting in only 50% loading capacity. A complete reduction in the loading was not observed because it is unlikely that every carboxylic acid was modified with an alkyne, allowing for some electrostatic interactions to remain. On the other hand, exterior modification of TMV showed no difference in Zn-EpPor loading, thus supporting interior loading.

Figure 10:
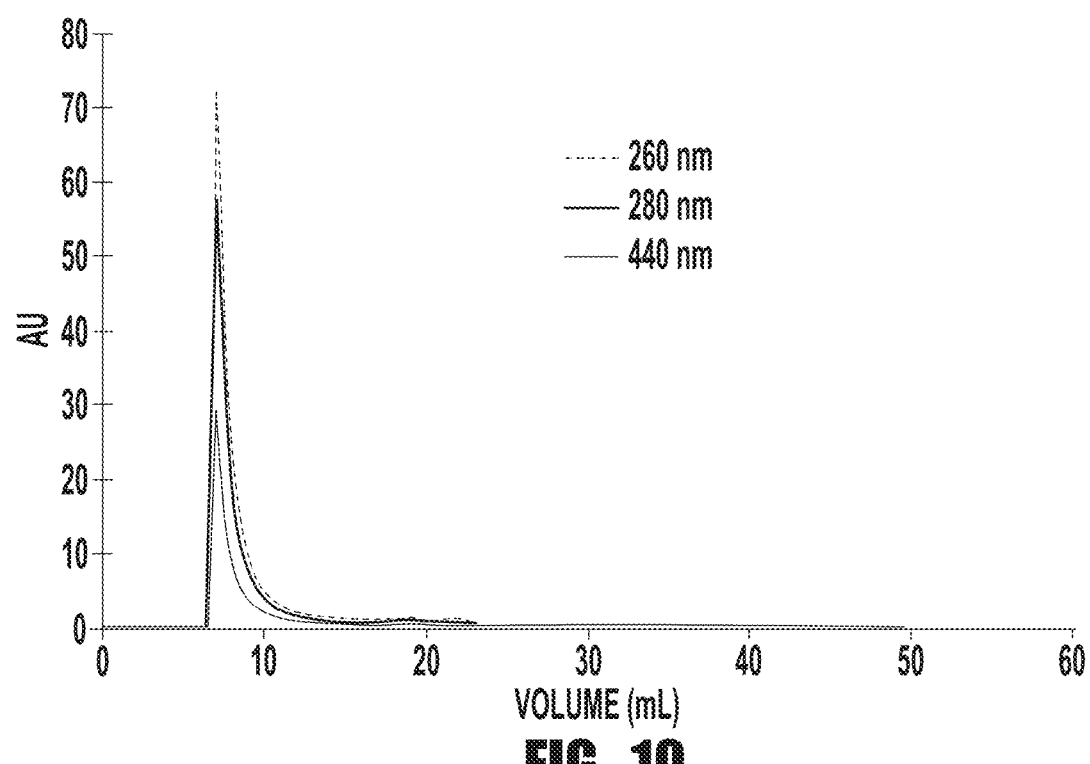
FIG. 10 provides a graph showing the stability of $_{Zn-EpPor}$TMV over time. TMV-Zn-EpPor stability was measured using size exclusion chromatography. $_{Zn-EpPor}$TMV stored at 4° C. for one month retains Zn-EpPor. The characteristic absorbance for TMV RNA (260 nm) and protein (280 nm) co-elute at the expected volume with the characteristic absorbance for Zn-EpPor (440 nm)

Lastly, the stability of the Zn-EpPorTMV complex in the dark and after light exposure was investigated. $_{Zn-EpPor}$TMV was kept in the dark or exposed to light—white light from a Vivitek D950HD projector (~10 mW cm$^{-2}$ at 430 nm) under a rectangle (10.5 cm×11 cm)—for 30 minutes and then analyzed using transmission electron microscopy (TEM). Light-exposed $_{Zn-EpPor}$TMV showed no apparent differences in their macromolecular structure compared to dark controls (FIG. 7F), indicating that the treatment with light did not impact the stability of the TMV carrier. Further, the ability of the TMV carrier to retain the Zn-EpPor compound during storage was assessed: $_{Zn-EpPor}$TMV was stored at 4° C. for one month in 0.01 M potassium phosphate buffer, pH 7.0, and subsequently analyzed using size exclusion chromatography. The elution profiles were consistent with an intact TMV carrier retaining the Zn-EpPor drug candidate (FIG. 10).

Cell Uptake and Intracellular Localization of $_{Zn-EpPor}$TMV in B16F10 Melanoma Photodynamic therapy (PDT) produces reactive oxygen species (ROS) that have very short half-lives. Therefore, to ensure that the ROS are able to exert their mechanism of action, it was important to confirm that Zn-EpPorTMV particles are able to bind to and/or be taken up by the cell; particles that remain in the extracellular space will not be effective for PDT.

Figure 8A:
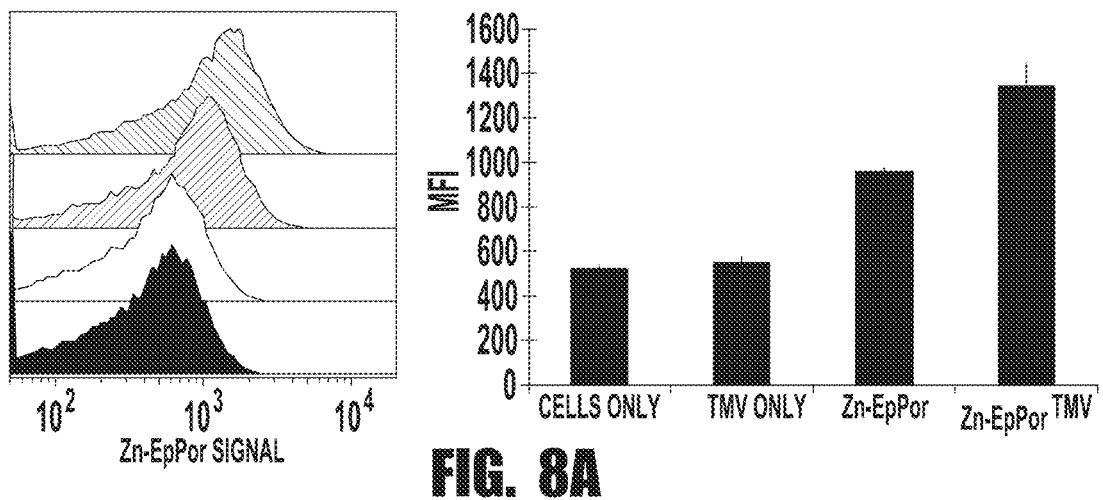
FIGS. 8A-8C provide graphs and images showing the $_{Zn-EpPor}$TMV interaction with B16F10 melanoma cells. (A) $_{Zn-EpPor}$TMV particles ($10^6$ particles/cell) or the corresponding amount of free Zn-EpPor or native TMV were incubated with B16F10 cells for 8 hours and analyzed using flow cytometry. (left) Representative histograms; (right) Statistical analysis (triplicates) and quantitative data show mean fluorescence intensity (MFI) of $_{Zn-EpPor}$TMV vs. free Zn-EpPor vs. unlabeled TMV vs. cells only control, *p<0.05; (B+C) Confocal microscopy indicates cellular uptake of $_{Zn-EpPor}$TMV. Nuclei are stained with DAPI and membranes are labeled with wheat germ agglutinin. Scale bar=10 microns FIGS. 9A and 9B provide a graph and images showing B16F10 response to $_{Zn-EpPor}$TMV and free Zn-EpPor. (A) Cell viability following 8 hour incubation with increasing doses of Zn-EpPor or $_{Zn-EpPor}$TMV and 30 minute illumination with white light (no cell killing was observed when cells were incubated in the dark, not shown). (B) Representative LIVE/DEAD images of B16F10 cells incubated with 5.0 µM free Zn-EpPor or $_{Zn-EpPor}$TMV. Cells only, TMV only, and dark controls exhibit no cell killing. The figures show live cells, stained with calcein AM and dead cells stained with ethidium homodimer-1; scale bar=200 microns.
Figure 8B:
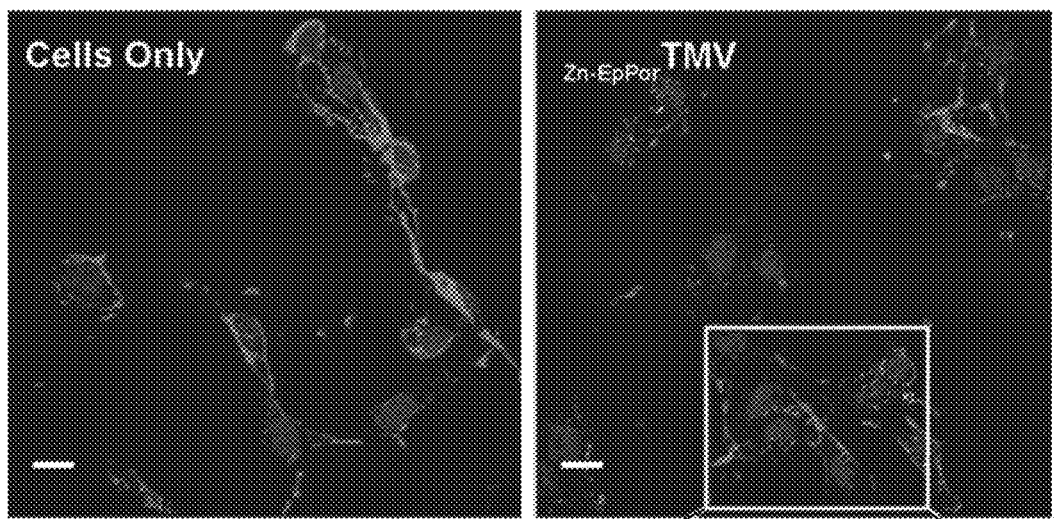
Figure 8C:
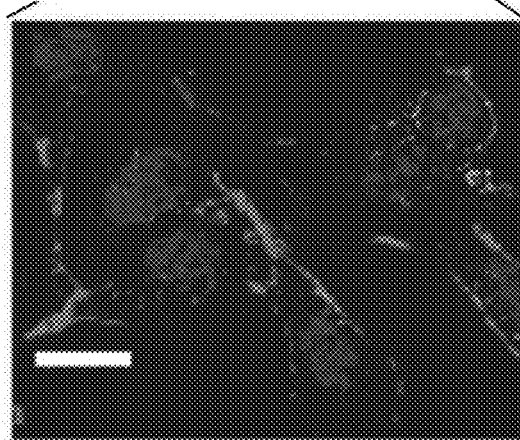

Cell binding and uptake of the PDT delivery system was measured using both flow cytometry and confocal microscopy. Data indicate that both free Zn-EpPor and $_{Zn-EpPor}$TMV are indeed taken up by B16F10 melanoma cells, with loading into the TMV carrier increasing cell uptake of Zn-EpPor, versus free drug alone. Cell uptake was measured as a function of Zn-EpPor fluorescence (FIG. 8A). Free Zn-EpPor had a mean fluorescence uptake (MFI) of 956, while $_{Zn-EpPor}$TMV exhibited 40% enhanced uptake, with a MFI of 1347 (p<0.05%). Unlabeled TMV did show an increase MFI compared to cells only control, indicating that the fluorescence observed is from the Zn-EpPor. These studies were complemented with confocal microscopy to determine the intracellular fate of Zn-EpPor delivered by TMV. Following an 8-hour incubation of B16F10 cells with $_{Zn-EpPor}$TMV particles, cells were fixed and stained with wheat germ agglutinin. Confocal fluorescence microscopy confirmed that Zn-EpPor is both taken up by the cells, and also dispersed throughout the cytoplasm (FIG. 8B), allowing it to exert their mechanism of action. The intracellular distribution of the Zn-EpPor drug was consistent with intracellular release of the cargo. We hypothesize that TMV is taken up and trafficked to the endolysosome, as previously reported. Wen et al., Bioconjugate chemistry, 26 (1), 51-62 (2015). The acidic endolysosomal compartment will result in protonation of the TMV's interior carboxylic acid resulting in drug release. Furthermore, it is expected that hydrolyases and proteases within the endolysosome will lead to degradation of the proteinaceous nanoparticle, further resulting in release of the Zn-EpPor, which escapes the lysosomes and is dispersed throughout the cytoplasm.

Therapeutic Efficacy of Zn-EpPorTMV Targeting Melanoma

Figure 9A:
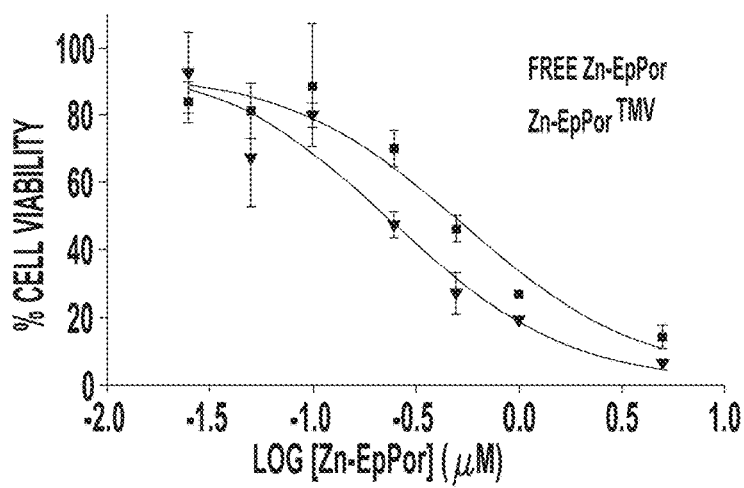

To evaluate efficacy in vitro, $_{Zn-EpPor}$TMV was studied in B16F10 melanoma versus free Zn-EpPor. Untreated cells and drug-free TMV carrier were used as controls. The TMV concentration was normalized to the drug-loaded concentration and corresponded to the highest amount of TMV used to determine the $IC_{50}$ curves (FIG. 9A). Drug candidates and controls were incubated with B16F10 cells for 8 hours, washed, and then exposed to white light from a Vivitek D950HD projector under a rectangle (10.5 cm×11 cm) for 30 minutes. Following illumination, cells were returned to the incubator for 48 hours. Cell viability was assessed using an MTT cell viability assay and analyzed using GraphPad Prism. The $IC_{50}$ values were determined as 0.54 µM and 0.24 µM for free Zn-EpPor and $_{Zn-EpPor}$TMV, respectively (FIG. 9A). Dark controls did not show any cell killing; neither did any of the controls lead to cytotoxicity. The increased efficacy of $_{Zn-EpPor}$TMV compared to that of free Zn-EpPor may be attributed to the increased cell uptake of Zn-EpPor due to its delivery by TMV.

Both free Zn-EpPor as well as $_{Zn-EpPor}$TMV performed comparably to previously reported pre-clinical and clinical photodynamic therapies. In B16F10, phthalocyanine-based drugs had $IC_{50}$ values between 1.10 and 1.25 µM, while the Japanese drug Talaporfin had an $IC_{50}$ of 8.50 µM. In a range of cell lines, including MCF-7, HeLa, and A2780, porphyrin-based photosensitizers had $IC_{50}$ values ranging from 0.45 to 5.0 µM. Additionally, it is of note that the clinically approved Photofrin is ineffective in pigmented melanoma due to inefficient light penetration in melanin-heavy cells, such as the B16F10 cell line. $_{Zn-EpPor}$TMV also shows comparable cell killing to other previously reported VNP-based photodynamic therapies. Photosensitizers, including C60 and other porphyrin-based sensitizers, have been attached to viral nanoparticles, including bacteriophages Qβ, MS2, and M13. These VNP-based systems also exhibited cell killing efficacy in the nano- to micromolar. Gandra et al., Small, 9 (2), 215-21 (2013); Cohen, B. A.; Bergkvist, M., Journal of photochemistry and photobiology. B, Biology, 121, 67-74 (2013).

Figure 9B:
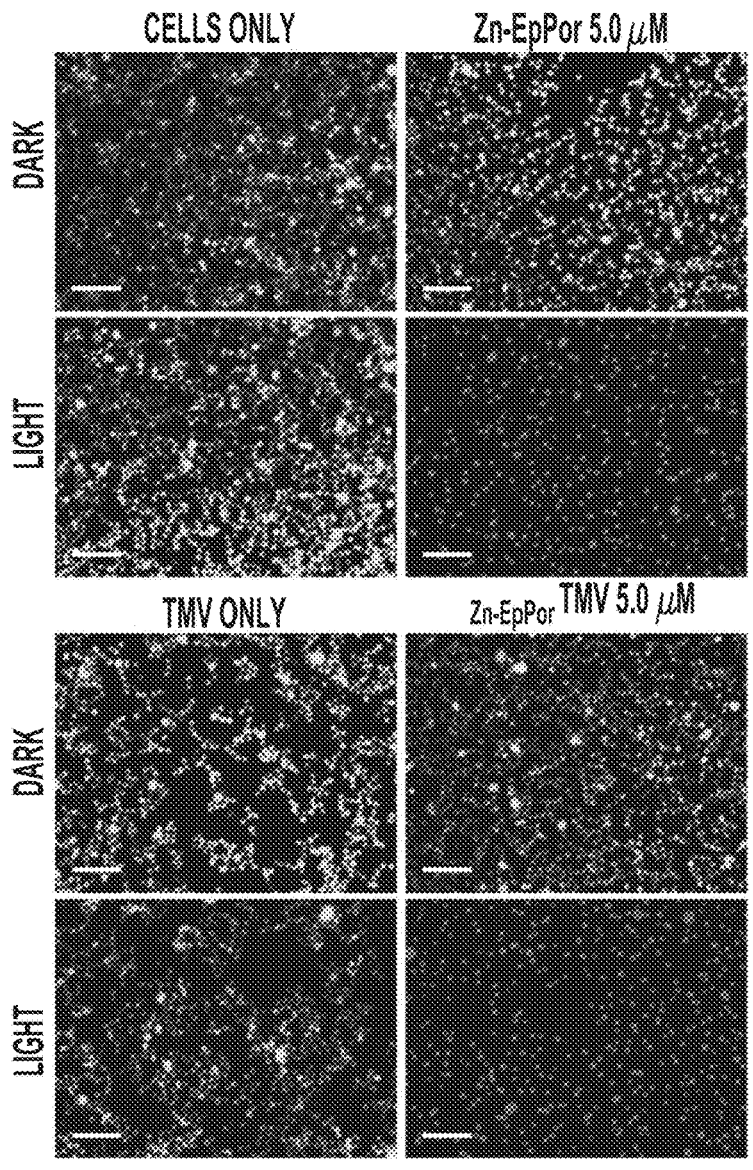

The MTT assay is based on a yellow tetrazolium dye that is reduced to purple formazan via NAD(P)H-dependent oxidoreductase enzymes. This reduction is highly dependent on cellular metabolism in the mitochondria and is not high in cells with low cellular metabolic activity. Liu et al., Journal of neurochemistry, 69 (2), 581-93 (1997). Because photosensitizers are known to impact the functionality of the mitochondria, the MTT assay may be compromised as a result of impaired mitochondrial activity. Therefore, LIVE/DEAD cell viability assays were performed to further confirm therapeutic efficacy and cell killing. Cells were incubated with 5.0 µM of free Zn-EpPor or $_{Zn-EpPor}$TMV, or corresponding controls, for 8 hours, washed, and illuminated for 30 minutes. This drug concentration was based on the MTT assay; it is over four times the $IC_{50}$ value in B16F10 melanoma and should give maximal cell killing. The LIVE/DEAD assay was applied the next day, imaged, and images were analyzed using ImageJ to determine percent cell viability (FIG. 9B). All samples kept in the dark, as well as cells only and TMV only controls exposed to light, exhibited high cell viability (98.32±0.53%). On the contrary, cells exposed to both Zn-EpPor or $_{Zn-EpPor}$TMV and light had 100% cell killing. It is important to note that although the MTT assay indicated an increased efficacy for $_{Zn-EpPor}$TMV versus free Zn-EpPor, the LIVE/DEAD assay in B16F10 cells showed 100% killing for both samples, as expected based on the 5 µM drug concentration.

CONCLUSION

In this study, a small molecule photosensitizer, Zn-EpPor, previously used in antimicrobial photodynamic inactivation studies was applied as a cancer therapeutic for the first time. Furthermore, to overcome translational challenges of PDT, such as poor solubility and drug targeting, the Zn-EpPor drug candidate was formulated as a nanoparticle therapeutic using the nucleoprotein components of tobacco mosaic virus (TMV). The drug formulation exhibited a good shelf-live, drug release during 1-month storage was not apparent, and the nanoparticles maintained structural integrity. The $IC_{50}$ was determined as 0.54 µM and 0.24 µM for free Zn-EpPor and $_{Zn-EpPor}$TMV, respectively. Overall, the $IC_{50}$ indicates that Zn-EpPor shows comparable efficacy compared to previously reported porphyrin-based PDT therapeutics. The $_{Zn-EpPor}$TMV particle proved to be stable and efficacious in vitro, improving upon the cell targeting, uptake, and killing versus free Zn-EpPor. Based on the biocompatibility and tumor homing properties of TMV, photosensitizer-TMV platforms such as $_{Zn-EpPor}$TMV may hold promise for application in PDT or combination therapies targeting melanoma or other cancers.

Experimental Section

Zn-EpPor Synthesis 5-(4-ethynylphenyl)-10,15,20-tris-(4-methylpyridin-4-ium-1-yl)porphyrin-zinc(II) triiodide (Zn-EpPor) was synthesized in a four-step procedure, as described previously. Feese et al., Biomacromolecules, 12 (10), 3528-39 (2011).

TMV Propagation

TMV was propagated in *Nicotiana benthamiana* plants. Infection was carried out using 100 ngmL$^{-1}$ TMV in 0.1 potassium phosphate (KP) buffer (pH 7.0); to promote the infectious process leaves were dusted with carborundum prior to mechanical inoculation. Leaves were collected 18-20 days post-infection and TMV was isolated using established procedures. Virus concentration was determined by UV/visible spectroscopy (εTMV=3.1 mLmg$^{-1}$ cm$^{-1}$).

Zn-EpPor Loading into TMV

Both wild-type TMV and a TMV-Lys mutant (TMVLys; T158K; Demir, M.; Stowell, M. H. B., Nanotechnology, 13 (4), 541-544 (2002)) were investigated for modification with Zn-EpPor. TMVLys was modified with an azide functional handle, followed by click chemistry using previously established methods. Bruckman et al., Chembiochem: a European journal of chemical biology, 9 (4), 519-23 (2008). Alternatively, TMV (1 mgmL$^{-1}$ final concentration, in 0.01 M KP buffer, pH 7.8) was incubated with a 6000 molar excess of Zn-EpPor, with agitation, overnight. TMV-Zn-EpPor was purified over a 40% (w/v) sucrose cushion using ultracentrifugation at 212,000×g for 3 hours at 4° C. temperature. Zn-EpPor-loaded TMV ($_{Zn-EpPor}$TMV) nanoparticles were analyzed using a combination of UV/visible spectroscopy, inductively-coupled plasma optical emission spectroscopy (ICP-OES), transmission electron microscopy (TEM), and size exclusion chromatography (SEC). To confirm that Zn-EpPor was indeed loaded into the central channel of TMV, chemically modified TMV was utilized in which either exterior or interior surface reactive groups were modified with biotin or alkynes to shield surface charges; the bioconjugation protocols were as previously described. Bruckman, M. A.; Steinmetz, N. F., Methods in molecular biology, 1108, 173-85 (2014).

UV/Visible Spectroscopy

The number of Zn-EpPor molecules per TMV nanoparticle was determined using both UV/vis spectroscopy and ICP-OES. Using the NanoDrop 2000 spectrophotometer, Zn-EpPor loading was determined using the Beer-Lambert law and the Zn-EpPor ($\varepsilon_{440nm}$=195,000 $M^{-1}$ $cm^{-1}$) and TMV ($\varepsilon_{260nm}$=3 $mLmg^{-1}$ $cm^{-1}$) molar absorptivity coefficients.

Inductively Coupled Plasma Optical Emission Spectroscopy (ICP-OES)

As a complementary method, ICP-OES was used to determine the number of Zn-EpPor molecules per TMV nanoparticle. This was achieved by quantification of the Zn:TMV ratio. To release Zn cations from the porphyrin backbone, $_{Zn-EpPor}$TMV was incubated in 1 M HCl for 2 hours at 60° C. Following incubation, the solution was diluted to 0.1 $mgmL^{-1}$ TMV and analyzed immediately at λ=202.548. The Zn concentration was determined using a calibration standard curve.

Size Exclusion Chromatography (SEC)

$_{Zn-EpPor}$TMV particles were analyzed by SEC using a Superose6 column and ÄKTA Explorer chromatography system (GE Healthcare). Samples (100 μL, 1 $mgmL^{-1}$) were analyzed at a flow rate of 0.5 mL $min^{-1}$ in 0.01 potassium phosphate buffer, pH 7.

Transmission Electron Microscopy

Transmission electron microscopy (TEM) was performed before and after light illumination to assess the stability of the drug delivery system. $_{Zn-EpPor}$TMV (1 $mgmL^{-1}$) was illuminated in a rectangle (10.5 cm×11 cm) under white light from a Vivitek D950HD projector (~10 mW $cm^{-2}$ at 430 nm) for 30 minutes (18.1 J $cm^{-2}$ at 430 nm). Control samples were kept in the dark for 30 minutes. Samples were then diluted to 0.1 $mgmL^{-1}$, placed on carbon-coated copper grids, and negatively stained with 2% (w/v) uranyl acetate for 5 min prior to imaging. Samples were analyzed using a Zeiss Libra 200FE transmission electron microscope operated at 200 kV.

Tissue Culture

B16F10 melanoma cells were purchased from ATCC and maintained in Dulbecco's modified Eagle's medium (DMEM) (Invitrogen) supplemented with 10% (v/v) fetal bovine serum (FBS) (Atlanta Biologicals) and 1% (v/v) penicillin-streptomycin (Invitrogen) and grown at 37° C. and 5% $CO_2$.

Flow Cytometry

Confluent B16F10 cells were removed using Hank's based cell dissociation buffer (ThermoFisher) and added to 96-well v-bottom plates (200 μL/well, 2.5×10⁶ cells/mL). Native TMV, free Zn-EpPor, or drug-loaded $_{Zn-EpPor}$TMV were added to wells (1×10⁶ particles/cell) in triplicate and incubated for 8 hours at 37° C. and 5% $CO_2$. Following incubation, cells were washed 2 times in FACS buffer (1 mM EDTA, 25 mM HEPES, 1% (v/v) FBS in PBS, pH 7.0) and fixed in 2% (v/v) paraformaldehyde in FACS buffer for 10 minutes at room temperature. Cells were washed 2 times, then resuspended in FACS buffer and analyzed on a BD FACSAria flow cytometer. Live cells were gated and 10,000 events were recorded; all experiments were carried out in triplicate. Data were analyzed on FlowJo 8.6.3 software.

Confocal Microscopy

Confluent B16F10 cells were removed using 0.05% (w/v) trypsin-EDTA and added to 24-well untreated plates with coverslips on the bottom (500 μL/well, 5×10⁴ cells/mL); cells were grown overnight. $_{Zn-EpPor}$TMV was added to wells (1×10⁶ particles/cell) and incubated for 8 hours at 37° C. and 5% $CO_2$. Following incubation, cells were fixed in DPBS containing 5% (v/v) paraformaldehyde and 0.3% (v/v) glutaraldehyde for 10 minutes at room temperature. Cell membranes were stained with wheat-germ agglutinin (WGA) conjugated to AlexaFluor488 (WGA-A488, Invitrogen) using 1 $\mu gmL^{-1}$ WGA-A488 in 5% (v/v) goat serum in DPBS for 45 minutes at room temperature. Cells were washed 3 times with DPBS in between each step. Coverslips were mounted onto slides using Fluoroshield with DAPI (Sigma) and sealed with nail polish. Slides were imaged using an Olympus FluoView FV1000 confocal laser scanning microscope, and the data were processed in ImageJ 1.47d.

Cell Viability

Cell viability was assayed using MTT and LIVE/DEAD assays. Confluent cells were removed using 0.05% (w/v) trypsin-EDTA, added to 96-well plates (100 μL/well, 2×10⁴ cells/mL), and grown overnight. Native TMV, drug loaded $_{Zn-EpPor}$TMV, vs. free Zn-EpPor were added to cells using 0.025, 0.05, 0.1, 0.25, 0.5, 1.0, and 5.0 μM Zn-EpPor; cells were incubated for 8 hours at 37° C. and 5% $CO_2$. Assays were done in triplicates and repeated at least twice. Following incubation, cells were washed twice to remove unbound drug and drug carriers, and then 100 μL medium was added. Samples were illuminated in a rectangle (10.5 cm×11 cm) under white light from a Vivitek D950HD projector (~10 mW $cm^{-2}$ at 430 nm) for 30 minutes (18.1 J $cm^{-2}$ at 430 nm). Control samples were kept in the dark for 30 minutes. After illumination, plates were incubated at 37° C. and 5% $CO_2$ for 48 hours. Cell viability was assessed using an MTT cell proliferation assay (ATCC); the procedure was as per manufacturer's recommendation. Alternatively, cell viability and cytotoxicity was determined using the LIVE/DEAD Viability/Cytotoxicity Kit for mammalian cells (ThermoFisher). The staining procedure was as per manufacturer's recommendation. Plates were imaged on a Zeiss Axio Observer Z1 motorized FL inverted microscope. Images were analyzed for percentage cell viability using ImageJ 1.47d.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. A photodynamic virus particle, comprising a tobacco mosaic virus particle associated with a zinc ethynyl porphyrin wherein the zinc ethynyl porphyrin is associated with the tobacco mosaic virus particle through electrostatic interaction.

2. The photodynamic virus particle of claim 1, wherein the zinc ethynyl porphyrin is associated to the interior of the virus particle.

3. The photodynamic virus particle of claim 1, wherein at least 20 zinc ethynyl porphyrin molecules are associated with the tobacco mosaic virus particle.

4. A method of treating cancer in a subject by administering to the subject a therapeutically effective amount of photodynamic virus particles comprising a tobacco mosaic virus particle associated with a zinc ethynyl porphyrin, and illuminating a cancer-bearing region of the subject to activate the photodynamic virus particles, wherein the zinc ethynyl porphyrin is associated with the tobacco mosaic virus particle through electrostatic interaction.

5. The method of claim 4, wherein the cancer is skin cancer.

6. The method of claim 4, wherein the cancer is melanoma.

7. The method of claim 4, wherein the photodynamic virus particle is administered together with a pharmaceutically acceptable carrier.

8. The method of claim 4, further comprising treatment of the subject with an additional type of anticancer therapy.

9. The method of claim 4, wherein the zinc ethynyl porphyrin is associated to the interior of the virus particle.

* * * * *